US009648890B2

(12) United States Patent
Nussinovitch et al.

(10) Patent No.: US 9,648,890 B2
(45) Date of Patent: May 16, 2017

(54) EDIBLE COATING FOR PLANT MATTER

(71) Applicant: Yissum Research Development Company of the Hebrew University of Jerusalem Ltd., Jerusalem (IL)

(72) Inventors: Amos Nussinovitch, Rehovot (IL); Tal Marmur, Tel Aviv (IL); Yonatan Elkind, Rehovot (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 14/387,242

(22) PCT Filed: Mar. 24, 2013

(86) PCT No.: PCT/IL2013/050287
§ 371 (c)(1),
(2) Date: Sep. 23, 2014

(87) PCT Pub. No.: WO2013/144961
PCT Pub. Date: Oct. 3, 2013

(65) Prior Publication Data
US 2015/0079248 A1    Mar. 19, 2015

Related U.S. Application Data

(60) Provisional application No. 61/617,179, filed on Mar. 29, 2012.

(51) Int. Cl.
*A23L 1/00* (2006.01)
*A23B 7/16* (2006.01)
*A01N 3/00* (2006.01)

(52) U.S. Cl.
CPC ............... *A23B 7/16* (2013.01); *A01N 3/00* (2013.01); *A23V 2002/00* (2013.01)

(58) Field of Classification Search
None
See application file for complete search history.

(56) References Cited

U.S. PATENT DOCUMENTS

| 4,021,262 | A | * | 5/1977 | Morales Guerrero | ............ C09D 191/06 106/271 |
| 4,649,057 | A | * | 3/1987 | Thomson | ............ A23D 7/0053 426/333 |

(Continued)

FOREIGN PATENT DOCUMENTS

| CN | 1466883 A | 1/2004 |
| CN | 101305749 | 11/2008 |

(Continued)

OTHER PUBLICATIONS

TB33: Postharvest Handling Technical Series: Waxing Fruits and Vegetables; Ministry of Fisheries, Crops and Livestock New Guyana Marketing Corporation; National Agricultural Research Institute: Technical Bulletin No. 33, Jun. 2004.*

(Continued)

*Primary Examiner* — Patricia George
(74) *Attorney, Agent, or Firm* — Vorys, Sater, Seymour and Pease LLP

(57) ABSTRACT

The present invention discloses composition and methods for reducing the weight loss and/or preserving the natural gloss of post-harvest edible plant matter. In particular, the methods comprising applying to the surface of the plant matter a composition comprising an edible wax having a melting temperature below 70° C.; a hydrocolloid; a fatty acid; an emulsifier; and water, wherein said edible wax is present in a weight percent ranging from about 10% to about 25% of the total weight of the composition.

12 Claims, 13 Drawing Sheets

(56) References Cited

U.S. PATENT DOCUMENTS

| | | | |
|---|---|---|---|
| 5,376,391 A * | 12/1994 | Nisperos-Carriedo | A23B 7/16 426/102 |
| 6,018,396 A | 1/2000 | Nussinovitsch | |
| 6,068,867 A | 5/2000 | Nussinovitch | |
| 6,299,915 B1 | 10/2001 | Nussinovitch | |
| 7,169,423 B2 | 1/2007 | Iverson | |
| 7,222,455 B2 | 5/2007 | Schrader | |
| 7,771,763 B2 | 8/2010 | Iverson | |
| 2004/0146617 A1 | 7/2004 | Schrader | |

FOREIGN PATENT DOCUMENTS

| | | |
|---|---|---|
| CN | 101642159 A | 2/2010 |
| CN | 101755899 A | 6/2010 |
| CN | 101884349 A | 11/2010 |
| WO | 01/03511 | 1/2001 |
| WO | 2010/124131 | 10/2010 |

OTHER PUBLICATIONS

Isaac: http://badgerandblade.com/vb/showthread.php/317453; online Nov. 1, 2012.*
Baldwin: Edible Coatings and Films to Improve Food Quality, Second Edition; CRC Press, Aug 24, 2011—Technology & Engineering—460 pages.*
Benard: WO/2001/003511: Method of Coating Food Products and a Coating Composition; Publication Date: Jan. 18, 2001.*
Ayranci and Tunc (2004) The effect of edible coatings on water and vitamin C loss of apricots (Armeniaca vulgaris Lam.) and green peppers (Capsicum annuum L.). Food Chemistry 87(3): 339-342.
Beaulieua et al., (2009) Extension of green bell pepper shelf life using oilseed-derived lipid films from soapstock. Industrial Crops and Products 30: 271-275.
Charles et al., (2008) Physiological basis of UV-C induced resistance to Botrytis cinerea in tomato fruit: II. Modification of fruit surface and changes in fungal colonization. Postharvest Biology and Technology 47(1): 21-26.
Chen and Nussinovitch (2000) Galactomannans in disturbances of structured wax—hydrocolloid-based coatings of citrus fruit (easy-peelers). Food Hydrocolloids 14(6): 561-568.
Chen and Nussinovitch (2000) The role of xanthan gum in traditional coatings of easy peelers. Food Hydrocolloids 14: 319-326.
Chen et al., (1995) Nature seal® delays yellowing of lemons. Proceedings of the Florida State Horticultural Society 108: 285-288.
Díaz-Pérez et al., (2007) Fruit size and stage of ripeness affect postharvest water loss in bell pepper fruit (Capsicum annuum L.). Journal of the Science of Food and Agriculture 87(1): 68-73.
Dijkink et al., (2004) Humidity control during bell pepper storage, using a hollow fiber membrane contactor system. Postharvest Biology and Technology 32(3): 311-320.
El Ghaouth et al., (1991) Use of chitosan coating to reduce water loss and maintain quality of cucumber and bell pepper fruits. Journal of Food Processing and Preservation 15(5): 359-368.
Goren et al., (2011) Photoselective shade nets reducing postharvest decay development in pepper fruits. Adv Horticultural Sci 25: 26-31.
Ha et al., (2007) A comparison of the carotenoid accumulation in Capsicum varieties that show different ripening colours: deletion of the capsanthin-capsorubin synthase gene is not a prerequisite for the formation of a yellow pepper. J Exp Bot 58(12): 3135-44.

Hagenmaier and Baker (1994) Wax Microemulsions and Emulsions as Citrus Coatings. Journal of Agricultural and Food Chemistry 42: 899-902.
Hagenmaier and Baker (1996) Edible coatings from Candelilla wax microemulsions. J Food Sci 61: 562-565.
Hershko and Nussinovitch (1998) The behavior of hydrocolloid coatings on vegetative materials. Biotechnol Prog 14 (5): 756-65.
Kester and Fennema (1986) Edible Films and Coatings: A Review. Food Technology 42: 47-59.
Lerdthanangkul and Krochta (1996) Edible coating effects on postharvest quality of green bell peppers. J Food Sci 61: 176-179.
Lima et al., (2010) New Edible Coatings Composed of Galactomannans and Collagen Blends to Improve the Postharvest Quality of Fruits—Influence on Fruit Gas Transfer Rate. Journal of Food Engineering 97:101-109.
Maalekuu et al., (2005) Characterization of physiological and Biochemical factors associated with post harvest water loss in ripe pepper fruit during storage. J Am Soc Horticultural Sci 130(5): 735-741.
Maalekuu et al., (2003) Quality evaluation of three sweet pepper cultivars after prolonged storage. Adv Horticult Sci 17:187-191.
Macrae et al., (1992) Carbohydrate metabolism during postharvest ripening in kiwifruit. Planta 188(3): 314-23.
Marcilla et al., (2009) Relationship between sensory and physico-chemical quality parameters of cold-stored 'Clemenules' mandarins coated with two commercial waxes. Spanish J Agri Res 7(1): 181-189.
Meir et al., (1995) Improvement of the postharvest keeping quality and color development of bell pepper (cv. 'Maor') by packaging with polyethylene bags at a reduced temperature. Postharv Biol Technol 5: 303-309.
Nussinovitch (2009) Biopolymer Films and Composite Coatings. In: Modern Biopolymer Science: Bridging the Divide between Fundamental Treatise and Industrial Application, 1st edition; edited by Stefan Kasapis, Ian T. Norton and Johan B. Ubbink. New York Academic Press, Elsevier Inc., pp. 295-326.
Nussinovitch et al., (1996) Gloss of fruits and vegetables. Lebensm.-Wiss. u.-Technol 29: 184-186.
Nussinovitch et al., (1996) Nondestructive measurement of peel Gloss and roughness to determine tomato fruit ripening and chilling injury. J Food Sci 61: 383-387.
Özden and Bayindirli (2002) Effects of combinational use of controlled atmosphere, cold storage and edible coating applications on shelf life and quality attributes of green peppers. Euro Food Res Technol 214: 320-326.
Park (1999) Development of advanced edible coatings for fruits. Trends Food Sci Technol 10: 254-260.
Perez-Gago et al., (2002) Effect of Lipid Type and Amount of Edible Hydroxypropyl Methylcellulose-lipid Composite Coatings Used to Protect Postharvest Quality of Mandarins cv. Fortune. Journal of Food Science 67(8): 2903-2910.
Sabularse et al., (2009) Preparation of nata de coco-based carboxymethylcellulose coating and its effect on the post-harvest life of bell pepper (Capsicum annuum I) fruits. Int J Food Sci Nutr 60(Suppl 7): 206-18.
Szczesniak AS (1983) In: Physical Properties of Food. Peleg M and Bagley EB (Editors) AVI Publishing Company, Inc., Westport, Connecticut (USA), pp. 11-12.
Villalobosa et al., (2005) Gloss and Transparency of Hydroxypropyl Methylcellulose Films Containing Surfactants as Affected by Their Microstructure. Food Hydrocolloids 19: 53-61.

* cited by examiner 1  2  3  4  5 6

EDIBLE COATING FOR PLANT MATTER

FIELD OF THE INVENTION

The present invention relates to a composition and methods for extending the shelf life of edible plant matter by reducing postharvest weight loss while preserving the external glossy appearance of the plant matter, in particular fruits and vegetables.

BACKGROUND OF THE INVENTION

Edible coatings, which are defined as thin layers of wax or other substances applied to the surface of food, have been employed for over 800 years to increase the shelf life of food. In the United States, wax coatings have been utilized commercially since 1930s, when oranges were coated with melted paraffin waxes. These early coatings were used to produce the appearance of a glossy skin. In recent years, coatings have been used to preserve attributes connected with fruit and vegetable quality and affording shelf-life extension involving a decrease in weight loss and respiration rate while providing glossy appearance and the possible prevention of damage induced by insect penetration (Nussinovitch in *Modern biopolymer science: bridging the divide between fundamental treatise and industrial application*, Kasapis et al. (Eds.), New York Academic Press, Elsevier Inc., 295-326, 2009).

Pepper fruit (*Capsicum annuum* L.) is naturally hollow and is therefore characterized by limited water reservoir capacity. Accordingly, the loss of small amounts of water may result in loss of freshness and firmness, a reduction in fruit quality, shelf life and market value (Maalekuu et al., J. Am. Soc. Horticult. Sci., 130, 735-741, 2005). The major factor shortening the postharvest life of bell peppers is water loss (Maalekuu et al., Adv. Horticult. Sci., 17, 187-191, 2003). Once the fruit is harvested, its tissue may rapidly dehydrate since the water potential ($\Psi$), which quantifies the water content of the surrounding air, is much lower than that of the plant tissue thus causing the diffusion of water from the fruit tissue to the environment. Consequently, postharvest shriveling of the fruit occurs (Dijkink et al., Postharvest Biol. Technol., 32, 311-320, 2004). Flaccidity, shriveling, wilting and decay are major problems that decrease marketability and consumer acceptance of postharvest bell pepper fruit. Flaccidity is also directly associated with the loss of water during storage when respiration as well as diffusion of water through the cuticle occur. Shriveling and wilting are processes which are evident in water loss of 5% or more. Hence, reduction of water loss, especially through diffusion through the cuticle, would help maintain textural quality and external appearance of the fruit thus improving its storage life.

Achieving water-saturated atmosphere around the fruit by individual-seal, shrink-wrap or modified-atmosphere packaging (MAP) has been employed. Bell peppers individually wrapped in plastic film showed marked reduction in weight loss and softening, which resulted in an extended shelf-life. Although individual-seal and MAP appeared to reduce bell pepper fruit moisture loss, a number of limitations inhibited commercial use. One limitation that has been encountered is the development of aerobic microorganisms due to water condensation caused by temperature fluctuations during storage or transportation. It was noted that film wrapping increased the incidence of bacterial soft rot in bell pepper compared to non-wrapped peppers. It was also shown that shrink-wrapped pepper developed higher populations of total aerobic microorganisms, yeasts, and molds as compared to non-wrapped peppers. Another limitation involved environmental apprehensions about the use of plastic materials. Hence, replacement of plastic films with edible or biodegradable materials is attractive from an environmental perspective.

The most common methods used nowadays for reducing water loss of postharvest fruit include lowering the temperature and/or raising the relative humidity (RH) of the storage environment. However, these storage environments can cause chilling injury, enhance disease development and increased incidence of fruit decay. In general, it is relatively difficult to preserve the quality of postharvest bell peppers as compared to other fruits, due to the peppers' sensitivity to low temperatures (<7° C.), water loss and rot development (Meir et al., Postharvest Biol. and Technol., 5, 303-309 1995).

The application of edible coatings and films in fruits and vegetables has received awareness worldwide for improvement of postharvest life (Lerdthanangkul et al., J. Food Sci., 61, 176-179, 1996; Conforti et al., Food Chem. Toxicol., 67, 1360-1363, 2002; Ozden et al., Euro. Food Res. Technol., 214, 320-326, 2002; Ayranci et al., Food Chem., 87, 339-342, 2004; Beaulieu et al., Indust. Crops and Products, 30, 271-275, 2009; Sabularse et al., Int. J. Food Sci. Nutri., 60, 206-218, 2009). However, despite their advantages, edible coatings for fruits can also adversely affect their quality. For example, an edible coating used to reduce the rate of water loss might interfere with fruit's respiration, resulting in off-flavors (Park, Trends Food Sci. Technol., 10, 254-260, 1999; Chen et al., Food Hydrocolloids, 14, 561-568, 2000). In addition, the surface gloss of food is a very important parameter since it reflects on its quality in the eye of the consumer. Bell peppers have very high natural gloss levels compared to other fruits (Nussinovitch et al., Lebensmittel-Wissenschaft und-Technologie, 29, 184-186, 1995). When very glossy surfaces, such as those of red bell pepper, are treated with available coating formulations, their natural shine may be diminished.

U.S. Pat. Nos. 6,299,915 and 6,068,867 to one of the inventors of the present invention disclose a hydrocolloid protective coating for food and/or agricultural products comprising dried hydrocolloid gel, one or more natural compounds isolated from the surface of said product or a compound substantially equivalent thereto and other optional additives. The protective coating provides improved protection of the product, thereby extending its shelf-life.

U.S. Patent application No. 2004/0146617 and U.S. Pat. No. 7,222,455 disclose methods for suppressing cracking, stem browning, and water loss in fruit or vegetables, such as cherries. The methods comprise applying to fruit or vegetables an amount of a wax emulsion comprising a matrix of complex hydrocarbons, one or more emulsifying agents, and water. In some embodiments, the wax emulsion comprises from about 0.125% to about 25% (weight/weight) of carnauba wax, from about 0.1% to about 16% (weight/weight) of oleic acid, and from about 0.03% to about 6% (weight/weight) of morpholine, and from about 53% to about 99.7% (weight/weight) of water.

Edible coatings on fruits can serve as gas or moisture barriers. They can help diminish moisture loss, and/or reduce fruit oxygen uptake from the environment and thus slow respiration. Edible coatings have been reported to be effective on various kinds of fruits and vegetables (U.S. Pat. Nos. 7,771,763 and 7,169,423). Chitosan coating reduced weight loss, respiration rate, loss of color, wilting, and fungal infection of bell pepper during storage at 13° C. and 20° C. at 85% RH (El Ghaouth et al., Journal of Food Processing and Preservation, 15 (5), 359-368, 1991). Although several attempts have been made to design edible coatings for bell pepper fruit, two main problems remained unsolved. First, the coating provided only ~4% reduction in the weight loss of the coated commodity and second, the coating reduced the natural gloss of the pepper.

There remains an unmet need in the art for an edible coating of bell pepper which provides an extension of its shelf life without impairing the natural gloss and taste thereof.

SUMMARY OF THE INVENTION

The present invention provides an edible hydrocolloid-wax based composition useful for coating plant matter, particularly a fruit or a vegetable having a high natural gloss and limited water reservoir capacity, the composition comprising an edible wax having a melting temperature below 70° C., a hydrocolloid, a fatty acid and an emulsifier. The composition of the present invention extends the shelf life of plant matter coated with the composition by reducing the plant's postharvest water loss while maintaining the natural glossy appearance of the plant matter, preferably by brushing or polishing the coated commodity.

The present invention is based in part on the unexpected finding that coating of fruits and vegetables having natural gloss with a composition comprising a wax having a melting temperature below 70° C. in an amount of at least 10% by weight of the composition and less that 1% of a non-gelling hydrocolloid, significantly reduced the postharvest water loss of the fruits and vegetables, without affecting their taste and only minimally affecting their natural gloss. Surprisingly, the compositions of the present invention reduced the weight loss of coated peppers by ~50% as compared to non-coated peppers, thus doubling the shelf life of coated peppers versus the non-coated ones. Although the natural gloss of the peppers was typically reduced by about 25% upon coating with the composition of the present invention, brushing of the peppers restored their natural shine, while maintaining the weight loss of the coated peppers significantly lower than the weight loss of the uncoated peppers.

The compositions of the present invention are highly advantageous as they restore the natural gloss of the post-harvest fruits and vegetables as well as significantly reduce their water loss and preserve their pleasing taste. It should be appreciated that by virtue of the specific combination of the ingredients of the compositions of the present invention, the three effects, i.e., restoration of the natural gloss, reduction of water loss, and preservation of the taste of the post-harvest fruits and vegetables, are achieved. Known coating compositions, although capable of restoring the natural gloss of post-harvest fruits and vegetables, often harm the pleasing taste of these fruits and vegetables. Thus, the compositions of the present invention provide, for the first time, means for coating post-harvest fruits and vegetables which restores their natural gloss, reduces their water loss, and preserves their pleasing taste, thereby extending their shelf-life without compromising their appealing appearance.

According to a first aspect, the present invention provides a composition for coating edible plant matter having a natural gloss, the composition comprising an edible wax having a melting temperature below 70° C., a hydrocolloid polymer, a fatty acid, an emulsifier and water, wherein the edible wax is present in an amount greater than 10% (w/w) and preferably equal or greater than 15% (w/w) of the total weight of the wet coating composition, wherein the amount of wax in the composition reduces the weight loss of the plant due to water evaporation while maintaining the pleasing taste and natural gloss of the plant matter as compared to a plant matter coated with the same composition with edible wax in an amount equal or lower than 10% or with an edible wax having a melting temperatures higher than 70° C. According to certain embodiments, the edible wax should constitute about 10 to 25% (w/w) of the weight of the wet coating composition and preferably between 15 and 25% (w/w) of the weight of the wet coating composition. Accordingly, after drying the coating on the surface of the edible plant, the edible wax will constitute between 55-80% (w/w) and preferably between 60-80% (w/w) of the dried composition. It is to be emphasized that after coating the plant matter, the wax-hydrocolloid coating is left to dry, preferably at room temperature. Preferably the drying of the coating results with a hydrocolloid-wax coating having low water activity. Typically the dried coating composition on the surface of the plant matter comprises up to 10% of water, preferably up to 5% of water, preferably, up to 3% of water and more preferably, up to 2% of water. Each possibility represents a separate embodiment of the invention.

According to some embodiments, the edible wax is having the melting temperature of up to 75° C. According to some embodiments, the edible wax is having the melting temperature of between 45 and 75° C. According to some embodiments, the edible wax is having the melting temperature of up to 70° C. According to some embodiments, the edible wax is having the melting temperature of between 50 and 70° C. According to some embodiments, the edible wax is selected from animal wax, insect wax, vegetable wax and mixtures thereof; each possibility represents a separate embodiment of the invention. According to some embodiments, the edible wax is an animal wax or an insect wax. In some preferred embodiments, the animal or insect wax is beeswax. In yet some other embodiments, the edible wax is a vegetable wax. Non limiting examples of vegetable waxes include candelilla wax, Japan wax, soy wax, bayberry wax, castor wax and mixtures thereof. Each possibility represents a separate embodiment of the present invention. According to still further embodiments, the edible wax is selected from mineral waxes, such as, but not limited to montan wax. According to yet a further embodiment, the edible wax is selected from petroleum waxes. According to some embodiments, petroleum waxes are selected from the group consisting of microcrystalline wax, paraffin wax, and mixtures thereof. Each possibility represents a separate embodiment of the present invention.

According to some embodiments, the amount of edible wax having a melting temperature below 75° C. and preferably below 70° C. in the composition is sufficient to provide the following parameters to an postharvest edible plant matter coated with the composition:

1. reduction of water loss;
2. preservation of the pleasing taste with no off-flavors; and
3. restoration of the natural gloss, as compared to an edible plant matter coated with a composition containing less than 10% (w/w) of wax in the wet composition or an edible plant matter coated with a composition containing same amount of wax, wherein the wax is having a melting point above 75° C.

The hydrocolloid polymer is typically present in an amount lower than 2% (w/w), preferably lower than 1% of the total weight of the wet coating composition. According to some embodiments, the weight percent of the hydrocolloid polymer in the composition is equal or lower than 0.5% (w/w), although the appropriate percentage of the hydrocolloid polymer used will be determined for the actual hydrocolloid polymer used, as is well known to one of skill in the art. After drying of the hydrocolloid-high wax composition, the hydrocolloid polymer weight percentage will correspondingly rise and, typically, will comprise a weight percent of 0.1 to 10% of the dry composition. Importantly, the hydrocolloid used in compositions and methods of the invention may influence the viscosity of the composition however it does not gellify the wet composition. Thus, according to some embodiments, the hydrocolloid polymer used may be selected from a non-gelling hydrocolloid polymer, a gelling hydrocolloid added to the composition in an amount lower than the amount sufficient for gellifing the composition or a gelling hydrocolloid added to the composition in the absence of a sufficient amount of cross-linking agents (such as for example potassium ions, or calcium ions) capable of causing the gellification of the composition.

In some embodiments, the hydrocolloid is a non-gelling hydrocolloid. In some embodiments, the non-gelling hydrocolloid is selected from the group consisting of locust bean gum (LBG), guar gum, xanthan gum and lambda-carrageenan. Each possibility represents a separate embodiment of the present invention. In some embodiments, the hydrocolloid is a gelling hydrocolloid used in an amount lower than the amount necessary for gelling the compositions of the present invention. Non-limiting examples of hydrocolloid suitable for use in the compositions of the present invention include: alginate, carrageenan, agar, agarose, arabinoxylan, carboxymethylcellulose, cellulose, curdlan, gelatin, gellan, β-glucan, pectin, starch, gum arabic, gum tragacanth, tamarind gum, fenugreek gum, cassia gum, tara gum. Each possibility represents a separate embodiment of the present invention. In an exemplary embodiment, the hydrocolloid is locust bean gum (LBG).

Without being limited by any specific theory or mechanism of action, the introduction of the hydrocolloid polymer into the wax composition altered the ordered structure of the wax in the composition after it has been dried on the surface of the plant matter, permitting better gas exchange with the atmosphere and thus resulting with a decrease in the production of off-flavor. As a result of this non-uniform or "imperfect" coating, the respiration of the coated plant matter is less disturbed and lower levels (relative to commercial coatings based on wax) of ethanol and acetaldehyde accumulate in the coated plant matter.

According to further embodiments, the fatty acid is typically present in the wet composition in the amount ranging from about 0.2 to about 10% (w/w). The emulsifier is typically present in the wet composition in an amount ranging from about 0.1 to 15% (w/w), preferably from about 0.1 to 10% (w/w), and more preferably from about 0.1 to 5% (w/w), and even more preferably from about 0.1 to 3% (w/w). According to certain embodiments, the emulsifier amount is lower than 2% (w/w) of the total weight of the wet coating composition.

In some embodiments, the fatty acid comprises an aliphatic chain of between 12 and 24 carbon atoms. In some embodiments, the aliphatic chain is saturated. In some embodiments, the aliphatic chain is un-saturated. Non limiting examples of fatty acids suitable for the coating composition of the present invention include oleic acid, stearic acid, palmitic acid, lauric acid, myristic acid, behenic acid, and isostearic acid. Each possibility represents a separate embodiment of the present invention. In an exemplary embodiment, the fatty acid is oleic acid.

In certain embodiment, the emulsifier is an edible emulsifier selected from non-ionic emulsifier, anionic emulsifier, and mixtures thereof. Each possibility represents a separate embodiment of the present invention. In some embodiments, the emulsifier enables to composition to be in a liquid form at room temperature. According to some embodiments, the emulsifier facilitates the solubility of the wax in the composition. According to some embodiments, the emulsifier served as a pH modifier of the composition. Non limiting examples of suitable emulsifiers include morpholine, ammonia, lecithin, ethylene glycol monostearate, ammonium lauryl sulfate, sodium steroyl-2-lactylate, potassium oleate, propylene glycol monostearate, sodium alkyl sulfate, polyglycol. Each possibility represents a separate embodiment of the present invention. In an exemplary embodiment, the emulsifier is morpholine.

In additional embodiments, the composition may further comprise a resin. In some embodiments, the resin may be selected from the group consisting of shellac, copal, damar, elemi and mixtures thereof. Each possibility represents a separate embodiment of the present invention. According to some embodiments, when the wax is a vegetable wax, an animal or insect derived resin (such as shellac) is added to the composition, preferably at a weight ratio of up to 5% of the total weight of the wet composition.

The composition of the present invention may further contain additional substances selected from the group consisting of antifoaming agents, preservative agents, adhesive agents, cross-linking agents, plasticizers, and surface-tension reducing agents. Each possibility represents a separate embodiment of the present invention. Exemplary additional substances include, but are not limited to polydimethylsiloxane (PDMS), potassium carbonate, sodium bisulfite, sodium benzoate, sodium propionate, calcium propionate, benzoic acid, potassium sorbate, polyethylene glycol, glycerol, propylene glycol, sorbitol, mannitol, high laurate canola oil (Laurical™), Astral R and HUMKOTE®. Each possibility represents a separate embodiment of the present invention.

According to some embodiments, the composition for coating edible plant matter comprises: from about 10% to about 25% (w/w) of edible wax, up to about 2% (w/w) of a hydrocolloid polymer, from about 0.5 to about 5% (w/w) of the fatty acid, and from about 0.3 to about 5% (w/w) of the emulsifier in the wet composition. According to some embodiments, the edible wax is beeswax. According to some embodiments, the hydrocolloid polymer is locust bean gum. According to some embodiment, the fatty acid is oleic acid. According to some embodiments the emulsifier is morpholine.

According to some embodiments, the composition for coating edible plant matter comprises: from about 10% to about 25% (w/w) of edible wax, up to about 1% (w/w) of a hydrocolloid polymer, from about 0.5 to about 5% (w/w) of the fatty acid, and from about 0.3 to about 5% (w/w) of the emulsifier in the wet composition. According to some embodiments, the edible wax is beeswax. According to some embodiments, the hydrocolloid polymer is locust bean gum. According to some embodiment, the fatty acid is oleic acid. According to some embodiments the emulsifier is morpholine.

According to some embodiments, the composition for coating edible plant matter comprises: about 10%-25% (w/w) of beeswax; up to about 1% (w/w) of hydrocolloid; about 0.2%-10% (w/w) of fatty acid; about 0.1%-15% (w/w) of emulsifier; and about 49%-89% water, of the total weight of the composition.

In one embodiment, the composition is applied to the edible plant matter postharvest.

In another embodiment, the edible plant matter comprises a fruit or a vegetable having naturally gloss appearance. In some embodiments, the edible plant matter comprises a fruit or a vegetable selected from the group consisting of peppers, eggplants cherries, berries plums and persimmons. Each possibility represents a separate embodiment of the present invention. In some embodiments, the peppers are selected from the group consisting of bell peppers, sweet peppers, chili peppers, and paprika peppers. Each possibility represents a separate embodiment of the present invention. In an exemplary embodiment, the plant matter is a bell pepper. In another embodiment, the edible plant matter comprises a fruit or a vegetable having small or limited water reservoir capacity. In particular embodiments, the edible plant matter comprises a fruit or a vegetable having from about 75% to about 95% (w/w) water content.

According to another aspect the present invention provides a method for reducing the weight loss and/or preserving the natural gloss of a post-harvest edible plant matter comprising step of applying to the surface of the plant matter a composition comprising: an edible wax having a melting temperature lower than 70° C.; a hydrocolloid polymer; a fatty acid; an emulsifier; and water, thereby coating the edible plant matter, wherein the edible wax is present in a weight percent ranging from 10% to 25% of the wet composition and from 50% to 85% (w/w) of the dried composition.

According to some embodiments, the composition is applied to the surface of the plant matter by rubbing the composition onto the surface of the plant, possibly by using of rubber gloves, dipping or immersing the edible plant matter in the composition, spraying the composition onto the edible plant matter, pouring the composition onto the plant matter, possibly when the plant matter is moving on a conveyor belt. Each possibility represents a separate embodiment of the present invention.

According to some embodiments, the application of the composition of the present invention to the surface of the plant matter is performed at room temperature (25° C.±10° C.). According to some embodiments, the composition is applied to the surface of the plant matter and/or to the stem of the plant matter when the temperature of the composition is between 35° C. to 70° C., preferably at a temperature of between 35° C. to 50° C. After applying the hydrocolloid-wax composition to the surface of the plant matter, the coating is left to dry on the surface of the plant matter, preferably at room temperature.

According to some embodiments, the method of the invention further comprises the step of brushing the coated edible plant matter. The brushing of the coated plant matter restores the glossy appearance of the plant matter to at least 80% of the natural gloss of uncoated plant matter, preferably to at least 85% of the natural gloss of the uncoated plant matter and most preferably to about 90% of the natural gloss of the uncoated plant.

Polishing or brushing the coating decreased its thickness and induced the redistribution of the wax on the surface of the plant matter which increased the gloss values of the coated plant matter. Polishing of a plant matter coated with a hydrocolloid-wax composition wherein the wax had a melting temperature below 70° C. (e.g. beeswax) resulted in a glossier appearance as compared to a plant matter coated with a hydrocolloid-wax composition wherein the wax has a melting temperature above 70° C. (e.g. carnauba wax). Without being limited by any theory or mechanism of action, the glossier appearance may result from the greater redistribution of the wax due to its relative softness.

According to some embodiments, the coating thickness prior to brushing is between 20 and 50 μm thick. According to some embodiments, the coating thickness is reduced by up to 50% upon brushing. According to some embodiments, the brushing of the coated plant matter is performed using a brush comprising natural fibers such as horse hair fibers. According to some embodiments, the brushing of the coated plant matter is performed using a brush comprising synthetic fibers such as nylon or polyethylene fibers. According to some embodiments the brush comprises horse hair fibers. According to some embodiments, the coated plant is brushed for up to 20 minutes, preferably between 1-10 minutes, at a brushing speed of about 100 to 300 rpm.

According to some embodiments, the method of the invention provides the extension of shelf life of edible plant matter by reducing the extent of weight loss during storage. According to some embodiments, the weight loss of a plant matter coated with the composition of the invention is reduced by at least 20%, preferably by at least 30%; preferably by at least 40%; and most preferably by about 50% as compared to an uncoated plant matter under same storage conditions. According to some embodiments, the method of the present invention provides the extension of the shelf life of the edible plant matter for between several days to several weeks beyond the shelf life of uncoated edible plant matter under the same storage conditions. According to some embodiments, the shelf life of an edible plant matter coated with the formulation of the invention is doubled as compared to the shelf life of an uncoated plant matter under the same storage conditions.

The methods of the present invention are particularly advantageous for the coating of edible plant matter comprising fruits or vegetables having small water reservoir capacity and/or to fruits or vegetables having a natural glossy appearance such as for example peppers, eggplants and persimmons. According to some currently preferred embodiments, the methods of the present invention suitable for coating peppers.

According to some additional preferred embodiments, the present invention provides a method for reducing the weight loss and/or preserving the natural gloss of a post-harvest edible plant matter comprising step of applying to the surface of the plant matter a composition comprising: beeswax; present in a weight percent ranging from 10% to 25% of the wet composition and from 50% to 85% (w/w) of the dried composition, a hydrocolloid polymer; a fatty acid and an emulsifier. According to yet additional preferred embodiments, the present invention provides a method for reducing the weight loss and/or preserving the natural gloss of a post-harvest pepper (such as a bell-pepper) comprising the step of applying to the surface of the pepper a composition comprising: beeswax; present in a weight percent ranging from 10% to 25% of the wet composition and from 50% to 85% (w/w) of the dried composition, a hydrocolloid polymer; a fatty acid and an emulsifier.

In another aspect, the invention provides a method for preparation of the hydrocolloid-high wax compositions useful for the coating of a plant matter, particularly fruit or vegetable having limited water reservoir capacity and high natural gloss, the method comprising the steps of: a) adding a hydrocolloid to preheated water having a temperature in the range from about 55° C. to about 95° C., more preferably from about 75° C. to about 85° C.; b) adding a fatty acid and an emulsifier to the mixture obtained in step a; c) adding molten wax to the mixture obtained in step (b).

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

(FIG. 1A) Engine (1), rotating brush (2), pepper/plate sample (3), lab jack adjusting handle (4); (FIG. 1B) Engine (1), coupling (2), aluminum tank (3), pepper (4), cylindrical brush (5), bearing (6).

(FIG. 6A) Average gloss of aluminum plate before coating (left), after coating with carnauba wax formulation (middle) and after brushing the coated plate for five minutes using a horse hair brush (right) at five different speeds; (FIG. 6B) Average gloss of aluminum plate after coating with carnauba wax formulation (left) and after brushing the coated plate for five minutes using a horse hair brush (right) at five different speeds. The letter above each column represents significant differences between treatments FIGS. 7A-7D. SEM micrographs of the three types of brush fiber samples.

DETAILED DESCRIPTION OF THE INVENTION

Figure 1A:
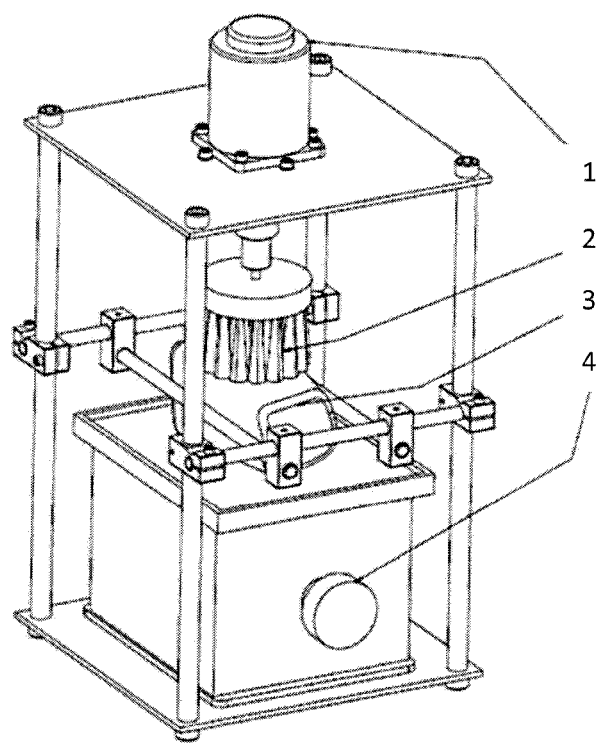
FIGS. 1A-1B. Brushing apparatus.

The present invention provides an edible hydrocolloid-wax based composition useful for coating a plant matter, particularly a fruit or a vegetable having a high natural gloss and limited water reservoir capacity, the composition comprising an edible wax having a melting temperature below 70° C., a hydrocolloid, a fatty acid and an emulsifier. The composition of the present invention extends the shelf life of a plant matter coated with the composition by reducing the plant's postharvest water loss while maintaining the natural glossy appearance of the plant matter, preferably by brushing or polishing the coated commodity.

The term "fruit or vegetable having a small water reservoir" as used herein refers to fruits or vegetables having from about 75% to about 90% (w/w) water content, for example, about 75%, about 80%, about 85%, or about 90% weight percent water. Each possibility represents a separate embodiment of the present invention. Fruit and vegetables having a small water reservoir include also hollow fruits or vegetables such as peppers having a small water reservoir. Additional non-limiting examples of such fruits and vegetables are eggplants, persimmons, grapes, mangos and papaya.

The term "glossy appearance", as used herein, refers to a physical property which is characteristic of the visual appearance of a plant matter and is very important for consumer acceptance. More specifically, gloss refers to the ability of the surface of a plant matter to reflect incident light giving a "shiny" or "glossy" appearance. Gloss can be measured in a variety of ways both visually and instrumentally. Specifically, gloss may be measured by a glossmeter which provides a quantifiable way of measuring gloss intensity. The measurement results of a glossmeter are related to the amount of reflected light from a black glass standard with a defined refractive index. The ratio of reflected to incident light for the specimen, compared to the ratio for the gloss standard, is recorded as gloss units. Typically, gloss may be measured at three measurement angles, i.e. 20°, 60° or 85° usually the angle is selected for a particular application based on the anticipated gloss range. As used herein, plant matter with natural gloss refers to a plant matter having a gloss value measured at 60° from a flat surface of 5 GU (gloss units) or greater, alternatively 7 GU or greater, alternatively at least 10 GU. According to some embodiments, glossy appearance refers to 60° gloss value of 12 GU or greater.

"Gloss Units (GU)" is a scaling based on a highly polished reference black glass standard with a defined refractive index having a specular reflectance of 100 GU at the specified coincident angle. This standard is used to establish an upper point calibration of 100 with the lower end point established at 0 on a perfectly matt surface.

The terms "restoring the glossy appearance", "restoring the gloss", "maintaining the glossy appearance" and "maintaining the gloss", as used herein, refer to achieving a gloss value which is at least 80% of the natural gloss of uncoated plant matter.

It has been previously shown that by applying a composition comprising a wax and a hydrocolloid on the surface of citrus fruits, postharvest water weight loss can be significantly reduced (S. Chen, A. Nussinovitch, Food hydrocolloids 14, 561-568, 2000). Compositions comprising a non-gelling hydrocolloid with edible wax, coated on a citrus surface provided a coating which decreased water evaporation rate while preventing fermentation and the formation of off-flavors. However, application of such composition to fruits or vegetables, having a naturally glossy appearance, impaired the natural gloss of the plant matter and reduced commercial attractiveness thereof.

It has now been found that increasing the edible wax concentration in the coating composition allowed an only minimal reduction in natural gloss of the coated plant matter. Performing appropriate brushing after applying the hydrocolloid—high wax compositions of the present invention restored the glossy appearance of the plant matter. Therefore, the composition of the present invention overcomes the disadvantages of known compositions by using a hydrocolloid-high wax coating which reduces water weight loss but does not impair the gloss and taste of edible plant matter.

The composition of the present invention comprises an edible wax. According to some embodiments, the composition of the present invention comprises at least 10% (w/w) of the edible wax. According to some embodiments, the composition comprises between about 10% and about 25% (w/w) edible wax, and preferably between about 15% and about 25%. For example about 15, about 16, about 17, about 18, about 19, about 20, about 21, about 22, about 23, about 24, or about 25 weight percent edible wax. Each possibility represents a separate embodiment of the present invention. The term "edible wax" as used herein refers to synthetic waxes that are suitable for human consumption, such as food-grade petroleum products, or natural waxes obtained from plants, insects (similar to honey bees) or animals. Non-limiting examples of vegetable waxes include candelilla wax, Japan wax, soy wax, castor wax, bayberry wax and mixtures thereof. Each possibility represents a separate embodiment of the present invention. Preferably, the edible wax is selected from animal or insect waxes such as beeswax. The edible wax may further be selected from mineral waxes, such as, but not limited to montan wax or from petroleum waxes, such as but not limited to, microcrystalline wax and paraffin wax. Preferably, the edible wax is selected from waxes having a melting temperature lower than 70° C., such as, but not limited to, beeswax having a melting temperature of between 62-64° C.

According to some embodiments, the wax comprises a mixture of waxes. According to some embodiments the mixture of waxes comprises at least one wax having a melting temperature lower than 70° C. According to some embodiments, a mixture of waxes comprises at least one wax having a melting temperature lower than 70° C. and at least one wax having a melting temperature above 70° C. According to some embodiments, the mixture of waxes comprises one or more waxes having a melting temperature lower than 70° C. present at a weight percent of at least 50% (w/w) of the total weight of waxes in the composition; alternatively, at least 60% (w/w) of the total weight of waxes in the composition; alternatively, at least 70% (w/w) of the total weight of waxes in the composition; alternatively, at least 80% (w/w) of the total weight of waxes in the composition; alternatively, at least 90% (w/w) of the total weight of waxes in the composition; alternatively, at least 95% (w/w) of the total weight of waxes in the composition; alternatively, at least 98% (w/w) of the total weight of waxes in the composition; alternatively, at least 99% (w/w) of the total weight of waxes in the composition. Non limiting examples of waxes having a melting temperature above 70° C. include: carnauba wax, rice bran wax, ouricury wax and esparto wax. According to one embodiment, the wax may comprise a mixture of beeswax and carnauba wax. According to another embodiment, the wax may comprise a mixture of beeswax and carnauba wax in a weight ratio ranging from about 1:10 to about 10:1.

The composition for coating edible plant matter comprises a hydrocolloid. The term "hydrocolloids" as used herein refers to water soluble polymers, of vegetable, animal, microbial or synthetic origin, that generally contain many hydroxyl groups and are capable of increasing the viscosity of the composition. The hydrocolloids of the present invention allow thickening of aqueous systems, without gelling thereof.

According to some embodiments, the hydrocolloid is a non-gelling hydrocolloid. According to some embodiments, the hydrocolloid may be a gelling hydrocolloid added to the composition at a concentration which is low enough so as not to cause the gellification of the composition. According to some embodiments, gelling hydrocolloids may be added at concentrations lower than 0.2% (w/w) of the wet composition, preferably, lower than 0.1% (w/w) of the weight of the wet composition. However, the appropriate percentage of the hydrocolloid polymer will be determined for the actual hydrocolloid used, as is well known to one of skill in the art. Suitable non-gelling hydrocolloids include, but are not limited to, locust bean gum (LBG), guar gum, xanthan gum, and gum tragacanth. Each possibility represents a separate embodiment of the present invention. Other non-gelling hydrocolloids within the scope of the present invention include, but are not limited to, lambda-carrageenan alkyl and hydroxyalkylcellulose, carboxymethyl cellulose, gum arabic, gum karaya, hydroxyethyl cellulose, hydroxypropylcellulose, tamarind gum and hydrolyzed gelatin. Additional hydrocolloids usable in the compositions of the present invention include, but are not limited to, tamarind gum, fenugreek gum, *cassia* gum, and tara gum. Suitable gelling hydrocolloids that may be used in non-gelling concentrations include but not limited to, agar, agarose, alginate, chitin, chitosan, curdlan, gellan, konjac mannan, pectin, and carrageenan.

Without being bound by any theory or mechanism of action, it is contemplated that the hydrocolloid increases the viscosity of the composition and forms discontinuity in the dried wax-based layer coating the surface of the plant matter, thereby preventing fermentation (e.g. anaerobic fermentation) and the formation or accumulation of off-flavors. The hydrocolloid may also serve as resistor to gases diffusion.

The composition of the present invention comprises a fatty acid. According to some embodiments, the fatty acid comprises an aliphatic chain of between 12 and 24 carbon atoms. Suitable fatty acids within the scope of the present invention include, but are not limited to, oleic acid, stearic acid, palmitic acid, lauric acid, myristic acid, behenic acid, and isostearic acid. Each possibility represents a separate embodiment of the present invention. Without being bound by any theory or mechanism of action, the fatty acid serves as a hydrophobic reservoir that decreases the water loss by evaporation thereby affording a decrease of the water evaporation rate. The fatty acid may further liquefy the formulation and enhance the glossy appearance of the plant matter when combined with the edible waxes of the composition.

According to some embodiments, the composition comprises from about 0.2 to about 10% (w/w) of a fatty acid. According to some embodiments, the composition comprises from about 0.2 to about 5% (w/w) of fatty acid.

According to some embodiments, the composition comprises from about 0.5 to about 4% (w/w) of fatty acid. According to some embodiments, the composition comprises from about 0.5 to about 3% (w/w) of fatty acid. According to some embodiments, the composition comprises from about 0.5 to about 2% (w/w) of fatty acid. Each possibility represents a separate embodiment of the present invention.

The composition of the present invention further comprises an emulsifier. Typically, the composition comprises from about 0.2 to about 15% (w/w) emulsifier. According to some embodiments, the composition comprises between 0.2 and 10%. According to some embodiments, the composition comprises between 0.2 and 5% of an emulsifier. According to some embodiments, the composition comprises between 0.5 and 3% of an emulsifier. Suitable emulsifiers include, but are not limited to edible non-ionic or anionic emulsifiers, such as morpholine, ammonia, lecithin, ethylene glycol monostearate, ammonium lauryl sulfate, sodium steroyl-2-lactylate, potassium oleate, propylene glycol monostearate, sodium alkyl sulfate, sodium oleate, sorbitan monostearate, oleic acid, and polyglycol. Each possibility represents a separate embodiment of the present invention. In certain embodiments, the emulsifier is a nitrogen containing emulsifier, e.g. morpholine.

The composition of the present invention can optionally contain additional substances selected from the group consisting of antifoaming agents, preservative agents, adhesive agents, cross-linking agents, plasticizers, and surface-tension reducing agents. Each possibility represents a separate embodiment of the present invention. Exemplary additional substances include, but are not limited to polydimethylsiloxane (PDMS), potassium carbonate, sodium bisulfite, sodium benzoate, sodium propionate, calcium propionate, benzoic acid, potassium sorbate, polyethylene glycol, glycerol, propylene glycol, sorbitol, mannitol, and HUMKOTE®. Each possibility represents a separate embodiment of the present invention.

According to the principles of the present invention, the addition of additional substances to the composition is performed in order to obtain a wax-hydrocolloid composition having desired properties such as, but not limited to desired viscosity, plasticity, hydrophobicity, shine, pH, and the like. For example, the additives may provide other characteristics, functions, or properties to the composition of the present invention, such as, but not limited to, disinfectant properties.

According to another aspect the present invention provides a method for reducing the weight loss and/or preserving the natural gloss of a post-harvest edible plant matter comprising step of applying to the surface of the plant matter a composition comprising: an edible wax having a melting temperature lower than 70° C.; a hydrocolloid polymer; a fatty acid; an emulsifier; and water, thereby coating the edible plant matter, wherein the edible wax is present in a weight percent ranging from 10% to 25% of the wet composition and from 50% to 85% (w/w) of the dried composition. According to some embodiments, the composition comprises: 10%-25% (w/w) of beeswax; up to 1% (w/w) of hydrocolloid; 0.2%-10% (w/w) of a fatty acid; 0.1%-15% (w/w) of an emulsifier; and 49%-89% of water of the total weight of the composition. According to other embodiments, the composition comprises: 15%-25% (w/w) of beeswax; up to 1% (w/w) of hydrocolloid; about 0.2%-3% (w/w) of a fatty acid; about 0.1%-5% (w/w) of an emulsifier; and 65%-84% water, of the total weight of the composition.

According to some embodiments, the composition is applied to the surface of the plant matter by rubbing the composition onto the surface of the plant, possibly by using of rubber gloves, dipping or immersing the edible plant matter in the composition, spraying the composition onto the edible plant matter, pouring the composition onto the plant matter, possibly when the plant matter is moving on a conveyor belt. Each possibility represents a separate embodiment of the present invention.

The composition may be applied at a certain temperature to afford a substantially uniform coating of the fruit or vegetable. According to some embodiments, the application of the composition of the present invention to the surface of the plant matter is performed at room temperature (25° C.±10° C.). According to some embodiments, the composition is applied to the surface of the plant matter when the temperature of the composition is between 35° C. to 70° C., preferably at a temperature of between 35° C. to 50° C. It will be recognized by one of skill in the art that the composition of the present invention is more easily applied in a liquid form. Accordingly, the composition may be applied at a temperature in which the edible wax is liquefied or partly liquefied.

After applying the hydrocolloid-wax composition to the surface of the plant matter, the coating is left to dry on the surface of the plant matter.

The present invention further provides a method of maintaining the external glossy appearance of the uncoated edible plant matter or restoring the external glossy appearance of the coated edible plant matter, the method comprising brushing the coated edible plant matter. It is contemplated that brushing is performed to increase the glossy appearance of the coated edible plant matter as compared to the glossy appearance of the coated unbrushed edible plant matter. The brushing of the coated plant matter restores the glossy appearance of the plant matter to at least 80% of the natural gloss of uncoated plant matter, preferably to at least 85% of the natural gloss of the uncoated plant matter and most preferably to about 90% of the natural gloss of the uncoated plant.

Without being bound by any theory or mechanism of action, polishing or brushing the coating decreases its thickness and induced the redistribution of the wax on the surface of the plant matter which increases the gloss values of the coated plant matter. According to some embodiments, the polishing of a coating comprising a wax having a melting temperature below 70° C., results with greater wax redistribution due to the wax's relative softness and results with a glossier appearance than the gloss obtained when a coating formulation comprises wax having a higher melting point.

According to some embodiments, the coating thickness prior to brushing is between 20 and 50 μm thick. According to some embodiments, the coating thickness is reduced by up to 50% upon brushing; accordingly the coating thickness after brushing is between about 10 to about 40 μm. According to some embodiments, the brushing of the coated plant matter is performed using a brush comprising natural fibers or bristles such as horse hair fibers, goat hair fibers, boar hair or bristles or pig hair. According to some embodiments, the brushing of the coated plant matter is performed using a brush comprising synthetic fibers such as nylon, polyethylene or rayon fibers. According to some embodiments, the brushing of the coated plant matter is performed using non-woven fabric or a non-woven high loft media. It is to be emphasized that the step of brushing the coated plant-matter is performed only after the hydrocolloid-wax coating composition has been fully dried. Drying of the coated plant matter is typically performed by allowing the coated plant matter to dry at room temperature. Alternatively, the coating composition may be left to dry or actively dried after its application to the surface of the plant matter by any method or under any conditions known in the art at the decision of the one skilled in the art. According to some embodiments the coated plant is brushed for up to 20 minutes, preferably between 1-10 minutes, at any brushing speed preferably from about 100 to 300 rpm, for example about 100 rpm, about 150 rpm, about 200 rpm, about 250 rpm, or about 300 rpm. Each possibility represents a separate embodiment of the present invention. According to some embodiments, the method of the invention provides the extension of shelf life of edible plant matter by reducing the extent of weight loss during storage. According to some embodiments, the method of the present invention provides the extension of the shelf life of the edible plant matter for between several days to several weeks beyond the shelf life of uncoated edible plant matter under the same storage conditions. According to some embodiments, the shelf life of an edible plant matter coated with the formulation of the invention is at least 20% higher than the shelf life of an uncoated plant matter under the same storage conditions; alternatively, at least 25% higher, alternatively at least 30% higher; alternatively at least 35% higher, alternatively at least 40% higher. According to some embodiments, the shelf life of an edible plant matter coated with the formulation of the invention is doubled as compared to the shelf life of an uncoated plant matter under the same storage conditions The methods of the present invention are particularly advantageous for the coating of edible plant matter comprising fruits or vegetables having small water reservoir capacity and/or to fruits or vegetables having a natural glossy appearance such as for example peppers, eggplants and persimmons. According to some currently preferred embodiments, the methods of the present invention suitable for coating peppers.

According to some additional preferred embodiments, the present invention provides a method for reducing the weight loss and/or preserving the natural gloss of a post-harvest edible plant matter comprising step of applying to the surface of the plant matter a composition comprising: beeswax; present in a weight percent ranging from 10% to 25% of the wet composition and from 50% to 85% (w/w) of the dried composition, a hydrocolloid polymer; a fatty acid and an emulsifier. According to yet additional preferred embodiments, the present invention provides a method for reducing the weight loss and/or preserving the natural gloss of a post-harvest pepper (such as a bell-pepper) comprising the step of applying to the surface of the pepper a composition comprising: beeswax; present in a weight percent ranging from 10% to 25% of the wet composition and from 50% to 85% (w/w) of the dried composition, a hydrocolloid polymer; a fatty acid and an emulsifier.

In another aspect, the invention provides a method for preparation of the hydrocolloid-high wax compositions useful for the coating of a plant matter, particularly fruit or vegetable having limited water reservoir capacity and high natural gloss, the method comprising the steps of:

a) Adding a hydrocolloid to preheated water having a temperature in the range from about 55° C. to about 95° C., preferably from about 75° C. to about 85° C.;

b) Adding a fatty acid and an emulsifier to the mixture obtained in step a;

c) Adding molten wax to the mixture obtained in step b.

According to some embodiments, step a is typically followed by vigorously stirring the solution for any length of time until the hydrocolloid is solubilized, typically between about 1 minute and about 30 minutes. The method further comprises adding a fatty acid and an emulsifier to the hot hydrocolloid solution. The preparation is followed by adding a previously molten wax to the solution and homogenizing the composition for any length of time, typically between about 1 minute and about 15 minutes. The composition is further stirred for the elimination of foam. According to some embodiments, the formation of foam may be reduced or even prevented by the addition of anti-foaming agents to the composition. According to some embodiments, the viscosity of the composition obtained is from about 5 to about 500 cP at a shear rate of 70 s$^{-1}$ and at a temperature of 25° C.

According to some embodiments, the wax-hydrocolloid composition is an emulsion. According to some embodiments, the wax-hydrocolloid composition is an emulsion stabilized by the emulsifier. According to currently preferred embodiments, the wax-hydrocolloid composition is an emulsion stabilized by morpholine. According to some embodiments, the emulsion is a oil in water emulsion.

As used herein and in the appended claims the singular forms "a", "an" and "the" include plural references unless the content clearly dictates otherwise. It should be noted that the term "and" or the term "or" is generally employed in its sense including "and/or" unless the content clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Materials and Methods

Formulations

The formulations comprising hydrocolloid and edible wax are presented in Table 1.

TABLE 1

| | Hydrocolloid-high wax composition formulations | | | | | | |
|---|---|---|---|---|---|---|---|
| Formulation | Wax (% w/w) | Locust bean gum (% w/w) | Oleic acid (% w/w) | Morpholine (% w/w) | Shellac (% w/w) | PDMS (% w/w) | Water (% w/w) |
| | Carnauba | | | | | | |
| 1 | 10 | 0.50 | 1.8 | 2.4 | 2.0 | — | 83.3 |
| 2 | 15 | 0.50 | 1.8 | 2.4 | 3.0 | — | 77.3 |

TABLE 1-continued

Hydrocolloid-high wax composition formulations

| Formulation | Wax (% w/w) | Locust bean gum (% w/w) | Oleic acid (% w/w) | Morpholine (% w/w) | Shellac (% w/w) | PDMS (% w/w) | Water (% w/w) |
|---|---|---|---|---|---|---|---|
| 3 | 18 | 0.45 | 1.6 | 2.2 | 3.6 | — | 74.2 |
| 3A | 18 | 0.50 | 1.6 | 2.2 | 3.6 | 0.01 | 74.1 |
| Beeswax | | | | | | | |
| 4 | 5 | 0.50 | 1.8 | 0.25 | — | — | 92.4 |
| 5 | 10 | 0.50 | 1.8 | 0.50 | — | — | 87.2 |
| 6 | 15 | 0.50 | 1.8 | 0.75 | — | — | 81.9 |
| 7 | 20 | 0.50 | 1.8 | 1.00 | — | — | 76.7 |

Formulations 1-3A comprise carnauba as an edible wax, wherein the wax weight percent in the compositions is in the range from 10 to 18% (w/w). Formulations 4-7 comprise beeswax as an edible wax, wherein the wax weight percent in the compositions is in the range from 5 to 20% (w/w).

Hydrocolloid-High Wax Formulation Preparation

Formulation 2 (Carnauba)

Locust bean gum (LBG; Sigma Chemical Co., St. Louis, Mo.) was added at 0.5% (w/w) to 77.3% (w/w) preheated water (85° C.) for 15 min with vigorous stirring. Oleic acid (1.8% w/w) (Aldrich Chemical Company, Inc., Milwaukee, Wis.) and 2.4% (w/w) morpholine (Sigma) were also added to the hot mixture, followed by the addition of 15 (w/w) of previously molten (95° C.) carnauba wax (Aldrich) and 3% (w/w) shellac (Safe-Pack, Inc., Kfar Saba, Israel).

Formulation 3 (Carnauba)

The coating formulation was prepared by adding Locust Bean Gum (LBG, Sigma) at (0.45%, w/w) to (74%, w/w) preheated water (85° C.) for 15 minutes with vigorous stirring. Oleic acid (1.6%, w/w) (Aldrich Chemical Company, Inc.) and morpholine (2.2%, w/w) (Sigma Chemical Co, St. Louis, Mo.) were added to the mixture, followed by the addition of 18% (w/w) of previously molten (95° C.) carnauba wax (Aldrich Chemical Company, Inc., Milwaukee, Wis.) and 3.6% (w/w) shellac (Safe-Pack, Inc., Kfar Saba, Israel). The formulation was homogenized by ultra-turrax (T-25, Janke and Kunkel, Germany) at 24,000 rounds per minute (rpm) for 5 minutes and stirred until no foam was observed.

Formulation 3A (Carnauba)

The coating formulation was prepared by adding Locust Bean Gum (LBG, Sigma) at (0.5%, w/w) to (74%, w/w) preheated water (85° C.) for 15 minutes with vigorous stirring. Oleic acid (1.6%, w/w) (Aldrich Chemical Company, Inc.) and morpholine (2.2%, w/w) (Sigma Chemical Co, St. Louis, Mo.) were added to the mixture, followed by the addition of 18% (w/w) of previously molten (95° C.) carnauba wax (Aldrich Chemical Company, Inc., Milwaukee, Wis.) and 3.6% (w/w) shellac (Safe-Pack, Inc., Kfar Saba, Israel). 0.01% (w/w) polydimethylsiloxane (PDMS; Dow Corning, Belgium) was added to the formulation. The formulation was homogenized by ultra-turrax (T-25, Janke and Kunkel, Germany) at 24,000 rounds per minute (rpm) for 5 minutes and stirred until no foam was observed.

Formulation 6 (Beeswax)

Locust bean gum (LBG; Sigma Chemical Co., St. Louis, Mo.) was added at 0.5% (w/w) to 82% (w/w) preheated water (85° C.) for 15 min with vigorous stirring. Oleic acid (1.8% w/w) (Aldrich Chemical Company, Inc., Milwaukee, Wis.) and 0.75% (w/w) morpholine (Sigma) were added to the hot mixture, followed by the addition of 15% (w/w) of previously molten (65° C.) beeswax (New Zealand Beeswax Ltd., Orari, South Canterbury, New Zealand). When necessary, an anti-foaming agent, such as polydimethylsiloxane (PDMS; Dow Corning, Belgium), was added to the formulation.

Formulation Properties Evaluation pH, °Brix and viscosity of the formulations 2, 3 and 6 were measured using digital pH meter (El-Hama, Israel)/(Hanna Instruments, Liemena, Padua, Italy), digital refractometer (PR-100, Atago, Japan) and the Brookfield DV-III rheometer (Brookfield, Mass., USA), respectively. All parameters were measured at room temperature of 25° C.

Plate and Fruit Samples Coating

Square polished aluminum plate (10× 10 cm) was coated by rubbing 40 µL of formulation 3 on the surface by hand (using rubber gloves) as described in Hagenmaier et al., J. Food Sci., 61: 562-565, 1996. The coated plate was left to dry at room temperature.

Red bell peppers, obtained from a local market, were washed in water and dried gently using very soft paper towels (Hogla, Hadera, Israel). Each fruit was cut and flattened into square shaped samples (10× 10 cm). Hydrocolloid-high wax coatings were applied by rubbing 40 µL of formulation 1 on the fruit sample surface by hand (using rubber gloves). Coated fruits were then left to dry at ambient temperature.

Fruit Coating

Red bell pepper fruit (Capsicum annuum cv. Cannon) (Zeraim, Gedera, Israel), were coated by manual rubbing with 300 µL of formulations 1-7 on the fruit sample surface by hand (using rubber gloves). Coated fruits were then left to dry at ambient temperature.

Plate and Fruit Samples Brushing

Following coating with formulation 3, each fruit sample was brushed individually by a custom made vertical brushing apparatus (FIG. 1A). Samples were brushed using three different types of brushes composed of horse hair, polyethylene or soft nylon fibers. Physical properties such as length and thickness of the brushes were measured using a digital caliper (Mitutoyo, Tokyo, Japan). Five different rotation speeds and three different brushing time periods were studied. The brushing procedure is summarized in Table 2 and the physical properties of the brushes are summarized in Table 3.

TABLE 2

Brushing protocol. Brushing procedure for aluminum plate and pepper fruit samples, with different brush types (horse hair, nylon, polyethylene), brushing time intervals (minutes) and rotating speed (round per minute).

| Brush type Horse/Nylon/Polyethylene Speed (rpm) | | | | | Time |
|---|---|---|---|---|---|
| 300 | 250 | 200 | 150 | 100 | (min) |
| Aluminum plate and pepper fruit | Aluminum plate | Aluminum plate and pepper fruit | Aluminum plate | Aluminum plate and pepper fruit | 1 |
| Aluminum plate and pepper fruit | Aluminum plate | Aluminum plate and pepper fruit | Aluminum plate | Aluminum plate and pepper fruit | 5 |
| Pepper fruit | | Pepper fruit | | Pepper fruit | 10 |

TABLE 3

Physical properties of the three brush types.

| Thickness (mm)* | Length (cm) | Brush type |
|---|---|---|
| 0.176 ± 0.03 | 5 | Horse hair |
| 0.284 ± 0.02 | 5 | Polyethylene |
| 0.174 ± 0.01 | 5 | Nylon |

*Each result is the average of 3 determinations ± standard deviation.

Fruit Brushing

Figure 1B:
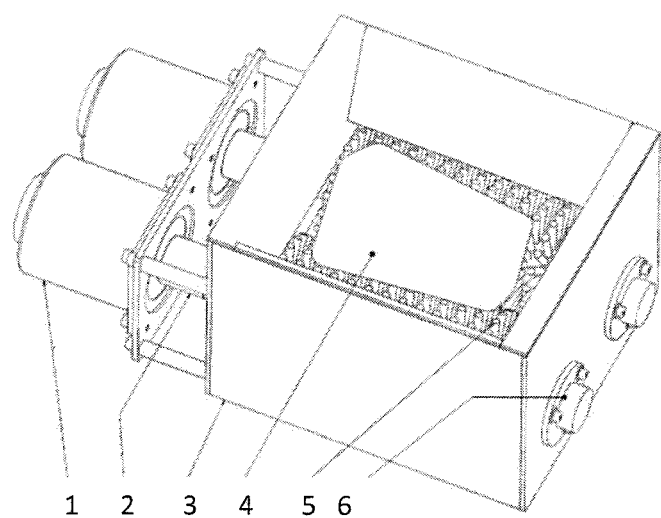

Following coating with formulations 1, 2, and 6 each pepper fruit was brushed individually by a custom made horizontal brushing apparatus (FIG. 1B). Fruits were brushed for 3 min at 100 rpm using two cylindrical horsehair brushes. Following coating with formulation 3 each pepper fruit was brushed individually by a custom made horizontal brushing apparatus (FIG. 1B for 5 min at 300 rpm using two cylindrical horsehair brushes.

Scanning Electron Microscopy (SEM)

SEM micrographs of the three types of brush fiber samples (polyethylene, soft nylon and horse hair) were obtained using a JEOL JSM-5410 LV SEM (Tokyo, Japan). Samples of the three types of brush fibers used in this study (horse, polyethylene and soft nylon) were gold coated (coating thickness of about 2 Å) by Polaron E5150 sputter coater (Hertfordshire, UK) following observation and photographing by JEOL JSM-5410 SEM (Tokyo, Japan).

Thickness Measurements

The thickness of the aluminum plate was measured for each treatment (uncoated, coated with formulation 3 and coated (with formulation 1) & brushed), using a coating thickness gauge, (Elcometer 355, Manchester, UK). Three measurements were obtained at different randomly selected places on the plate surface. Results are provided as mean±standard deviation (SD).

Weight Loss as a Function of the Wax Weight Percent in Formulation (Test Group A)

Test group A containing fifteen (15) red bell pepper fruit (*Capsicum annuum* cv. Cannon) (Zeraim, Gedera, Israel) was used to compare weight-loss rates as a function of the wax weight percent in formulations. Since weight loss is influenced by fruit size and surface area (Díaz-Pérez et al., J. Sci. Food and Agri., 87, 68-73, 2007), the peppers chosen for this study were of about the same size with an average weight of 195±22 g. The peppers were divided into seven treatment groups as follows: (1) uncoated control, (2) coated with formulation 1 (10% (w/w) carnauba formulation), (3) coated with formulation 2 (15% (w/w) carnauba formulation), (4) coated with formulation 4 (5% (w/w) beeswax formulation), (5) coated with formulation 5 (10% (w/w) beeswax formulation), (6) coated with formulation 6 (15% (w/w) beeswax formulation), and (7) coated with formulation 7 (20% (w/w) beeswax formulation). Each fruit was weighed (±0.01 g) every 24 hours for 7 days using a STANDARD Series 165 BJ1000C balance (Precisa Gravimetrics AG, Dietikon, Switzerland). The scale was attached to a computer and data were collected using BALINT V5.00 software (Balance interface for Windows, Precisa Instruments AG, Dietikon, Switzerland). Results are presented as average $(W_0-W_t) \times 100/W_0$, where $W_0$ is the weight at time zero (i.e. initial weight) and $W_t$ is the pepper's weight after elapsed time t. All peppers were stored at 21° C. and 50% RH. The vapor pressure deficit (VPD), which is the difference between the amount of moisture in the air and the amount of moisture the air can hold when it is saturated, was 1.24 kPa. Pictures of the peppers were taken during storage using a digital camera (Nikon Coolpix 600, Tokyo, Japan).

Weight Loss as a Function of the Wax Type and Brushing (Test Group B)

Test group B containing seventy five (75) red bell pepper fruit (*Capsicum annuum* cv. Cannon) (Zeraim, Gedera, Israel) was used to evaluate the effect of the wax type and brushing on the weight-loss rate. The peppers chosen for this study were of about the same size with an average weight of 262±17 g. The peppers were divided into five treatment groups as follows: (1) uncoated control, (2) coated with formulation 6 (15% (w/w) beeswax formulation), (3) coated with formulation 6 followed by brushing, (4) coated with formulation 2 (15% (w/w) carnauba wax formulation), and (5) coated with formulation 2 followed by brushing. Each fruit was weighed (±0.01 g) every 24 hours for 7 days using a STANDARD Series 165 BJ1000C balance (Precisa Gravimetrics AG, Dietikon, Switzerland). The scale was attached to a computer and data were collected using BALINT V5.00 software (Balance interface for Windows, Precisa Instruments AG, Dietikon, Switzerland). Results are presented as average $(W_0-W_t) \times 100/W_0$, where $W_0$ is the weight at time zero (i.e. initial weight) and $W_t$ is the pepper's weight after elapsed time t. All peppers were stored at 21° C. and 50% RH. The vapor pressure deficit (VPD), which is the difference between the amount of moisture in the air and the amount of moisture the air can hold when it is saturated, was 1.24 kPa. Pictures of the peppers were taken during storage using a digital camera (Nikon Coolpix 600, Tokyo, Japan).

Gloss Measurements (Test Group C)

Gloss of pepper fruit samples and aluminum plates that were coated with formulation 3 were examined using a flat surface hazemeter, capable of measuring gloss at coincident angles of 20° and 60° (Novo-Haze, Rhopoint Instrumentation Ltd., Germany). The results were recorded in gloss units (GU). A highly polished plane surface of black glass served as a standard having arbitrarily assigned gloss value of 100 at different coincident angles. Gloss measurements were performed on the same sample when uncoated, coated and coated & brushed. Each measurement contained three readings taken at different randomly selected points on the sample surface. All measurements were performed at room temperature. Results are provided as the arithmetic mean±SD. Pepper fruit surface samples from each treatment with formulation 3 (uncoated, coated and coated & brushed) were photographed using a research Grade Leica DMLM microscope.

Gloss Measurements (Test Group D)

Test group D containing forty eight (48) red bell pepper fruit (*Capsicum annuum* cv. Cannon) (Zeraim, Gedera, Israel) was used for the gloss measurements. The peppers were divided into three treatment groups as follows: (1) uncoated control, (2) coated with formulation 6 (15% (w/w) beeswax formulation), and (3) coated with formulation 6 followed by brushing. Average gloss for each treatment was measured by two types of glossmeters.

The first glossmeter was a flat-surface glossmeter (407 Statistical Glossmeter; Elcometer, Rochester Hills, Mich.) capable of measuring gloss at three angles: 20°, 60° and 85°. Eight peppers from each treatment were cut into flat square samples (5× 10 cm) using a sharp surgical blade (Bar-Naor Ltd., Ramat Gan, Israel). Results were recorded in gloss units (GU), which are relative to a highly polished plane surface of black glass with a gloss value of 88.9, 93.5 and 99.7 GU at 20°, 60° and 85°, respectively, which served as the standard.

The second glossmeter was a curved-surface glossmeter (U.S. Pat. No. 6,018,396) which illuminates the pepper with a light beam from a helium-neon laser at an incident angle of 60°. A semi-conductive plate collects all of the reflected light from the surface of the peppers. A video recorder (Sony Handycam video Hi8, Tokyo, Japan), positioned directly facing the plate, was used to record the images. The recorded images were relayed to a computer where they were analyzed by a special computer program which translated them into a goniophotometric curve of light intensity (arbitrary units) vs. distance or light scattering (pixels). The widths of the curves at half-maximum (50% intensity) were measured as an indicator of gloss (Nussinovitch et al., J. Food Sci., 61, 383-387, 1996). This apparatus permits measurements of whole fruits, i.e. it is a non-destructive procedure. The measured object can be placed inside the measuring apparatus without cutting it or, when needed, cut samples can be used. Twelve (12) whole (non-cut) peppers from each treatment were measured (n=36). Results were recorded in average curve widths at 50% intensity.

Gloss Evaluation (Test Group E)

Test group E contained nine (9) peppers, which were divided into three treatment groups (n=3) as follows: (1) uncoated control, (2) coated with formulation 3 (18% (w/w) carnauba formulation), and (3) coated with formulation 3 followed by brushing. Each member of the evaluation panel received all nine peppers and was asked to rank them by their glossy appearance (1—the least glossy appearance, 9—the glossiest appearance).

Roughness (Test Group D)

The roughness measurements were performed on surface samples (5× 10 cm) cut with a sharp surgical blade from four peppers from each treatment group in test group D, ((1) uncoated control, (2) coated with formulation 6 (15% (w/w) beeswax formulation), and (3) coated with formulation 6 followed by brushing) every 48 hours for 7 successive days using a portable surface-roughness tester (Surftest-301, Mitutoyo Corp., Tokyo, Japan). Each measurement tested a 7.5-mm path. Results were recorded as $R_a$ and $R_z$ where $R_a$ is the arithmetic average of the absolute values of the distance between the arithmetical mean line and the roughness profile (y) within the sampling length (lm) calculated using equation (1); and $R_z$ is the arithmetic average of the single peak-to-valley heights (Z) of five adjacent sampling lengths calculated using equation (2). Both $R_a$ and $R_z$ are provided in micrometers. Every measurement consisted of three readings taken along randomly chosen paths on the sample surface. All measurements were performed at room temperature. Results are provided as arithmetic mean±standard deviation (SD).

$$Ra = \frac{1}{lm}\int_0^{lm} |f(y)| dx \quad (1)$$

$$Rz = \frac{Z1 + Z2 + Z3 + Z4 + Z5}{5} \quad (2)$$

Color (Test Group F)

Test group F containing ten (10) red bell pepper fruit (*Capsicum annuum* cv. Cannon) (Zeraim, Gedera, Israel) was used for color evaluation. The peppers were divided into five treatment groups as follows (n=2): (1) uncoated control, (2) coated with formulation 6 (15% (w/w) beeswax formulation), (3) coated with formulation 6 followed by brushing, (4) coated with formulation 2 (15% (w/w) carnauba wax formulation), and (5) coated with formulation 2 followed by brushing. The colors of peppers from each treatment group were measured every 24 hours for 7 successive days using Minolta Color Meter CR200 (Osaka, Japan). Prior to the measurement, the instrument was calibrated with a white (standard surface) plate. Surface pigmentation variations for each pepper were compensated for by recording the average of three readings taken at random positions on the pepper's surface. Color changes were assessed by three parameters: L* represents the lightness of the sample and ranges from black (L*=0) to white (L*=100), a* represents the red-green axis and ranges from −60 for green to +60 for red, and b* represents the yellow-blue axis and ranges from −60 for blue to +60 for yellow (Hutchings, Food color and Appearance, Gaithersburg, Md.: Aspen Publishers, $2^{nd}$ Ed., 227-265, 1999). Results were recorded as average L*, a*, b* values±SD.

Mechanical Properties (Test Group D)

The firmness of four bell peppers from each treatment group in test group D ((1) uncoated control, (2) coated with formulation 6 (15% (w/w) beeswax formulation), and (3) coated with formulation 6 followed by brushing), was measured every 48 hours for 7 days by performing puncture tests using an Instron Universal Testing Machine (UTM) Model 5544 (Instron Engineering Corp., Canton, Mass.) equipped with a 50 N load cell. Each fruit was punctured using a 3-mm diameter punch at a deformation rate of 10 mm $min^{-1}$. The UTM was connected to an IBM-compatible personal computer with a card. Using "Merlin" software (Instron), data acquisition and conversion of the Instron's continuous voltage vs. time output into digitized force vs. deformation relationships was performed. Results are provided as the arithmetic mean±SD.

Microscopy (Test Group D)

Pepper fruit surface samples (1× 1 cm) cut with a sharp surgical blade from each treatment group in test group D, ((1) uncoated control, (2) coated with formulation 6 (15% (w/w) beeswax formulation), and (3) coated with formulation 6 followed by brushing), were photographed (20× magnification) on the first day of storage using the digital camera accessory of the light microscope (Leica DMLM, Wetzlar, Hesse, Germany).

Simulations of Storage and Marketing Conditions (Test Groups G and H)

Test groups G and H each containing ninety six (96) red bell pepper fruit (*Capsicum annuum* cv. Cannon) (Zeraim, Gedera, Israel) were used for simulation of storage and marketing conditions. In each test group the peppers were divided into three treatment groups (n=32) as follows: (1)

uncoated control, (2) coated with formulation 6 (15% (w/w) beeswax formulation), and (3) coated with formulation 6 followed by brushing. Group G was stored at 7° C. and 95% RH (VPD=0.05 kPa) for 3 weeks and group H was stored for 5 weeks under the same temperature and RH conditions. After their respective storage periods, the peppers were transferred to 20° C. and 75% RH (VPD=0.58 kPa) for 3 days, simulating supermarket conditions (Goren et al., Adv. Horticultural Sci., 25, 26-31, 2011). Each fruit was weighed before and after cool storage and once again after the 3 days of storage at room temperature. Weight loss was recorded and analyzed as described hereinabove.

Sensory Evaluation

Five sensory evaluation tests were performed on uncoated and treated (formulations 2 & 6) red bell peppers.

1. Initial Taste Evaluation

Taste of the pepper fruits was evaluated by a panel of 18 members on the first day of the study. The aim of this first taste evaluation test was to study whether the 15% (w/w) beeswax coating formulation (formulation 6) changes the flavor of the fruit. Thus, a blind triangle test was performed, in which each panel member received three fruit samples: two uncoated and one coated fruit, or two coated and one uncoated fruit. The panel member had to distinguish the dissimilar sample based only on taste.

2. Gloss Evaluation

The aim of the gloss evaluation was to determine whether the coated commodities will differ from the uncoated ones in the eyes of the consumer. Each panel member received six peppers, two from each from each treatment group in test group D, ((1) uncoated control, (2) coated with formulation 6 (15% (w/w) beeswax formulation), and (3) coated with formulation 6 followed by brushing), and was asked to rank the fruits according to their gloss, with 1 denoting the least glossy appearance and 6 denoting the glossiest pepper appearance (Marcilla et al., Spanish J. Agri. Res., 7, 181-189, 2009).

3. Taste Evaluation after Storage

After 1 week in storage at 21° C. and 50% RH, additional sensory evaluation test was performed by a 13-member panel. Another taste test was performed to determine whether coating the fruit with beeswax had created off-flavors as a result of changes in the normal respiration process during storage. A triangle test was performed as described hereinabove and in addition, the testers were asked to describe the taste that distinguished the chosen sample from the other two.

4. Sensory Firmness Evaluation after Storage

In addition, a firmness evaluation test was performed after 1 week in storage at 21° C. and 50% RH. The panel members were asked to rank six peppers according to their hardness, with 1 being the softest and 6 being the firmest.

5. Final Sensory Evaluation

A final sensory evaluation test was designed to analyze consumer preferences considering all quality parameters together. This test consisted of 10 peppers, two from each treatment group in test group B ((1) uncoated control, (2) coated with formulation 6 (15% (w/w) beeswax formulation), (3) coated with formulation 6 followed by brushing, (4) coated with formulation 2 (15% (w/w) carnauba wax formulation), and (5) coated with formulation 2 followed by brushing.) Each panel member was asked to choose the three peppers that he/she would buy at the supermarket.

Statistical Analysis

Statistical analyses were conducted with JMP software (SAS Institute, 2007, Cary, N.C.), including three-way ANOVA t-tests and Tukey-Kramer Honestly Significant Difference (HSD) test for comparisons of means, with $p \leq 0.05$ being considered significant.

Example 2

Properties of Formulations 2, 3 and 6

The properties of formulations 2, 3 and 6 were evaluated. The measured pH, °Brix and viscosity are presented in table 4.

TABLE 4

Physical properties of the hydrocolloid-high wax formulations

| Formulation | pH | °Brix | Viscosity at 70 1/sec shear rate (cP) |
|---|---|---|---|
| 2 | 9.09 | 28.1 | 195 |
| 3 | 8.90 | 15.0 | 220 |
| 6 | 8.88 | 19.1 | 85 |

Example 3

Thickness of Coating (Formulation 3)

Figure 2A:
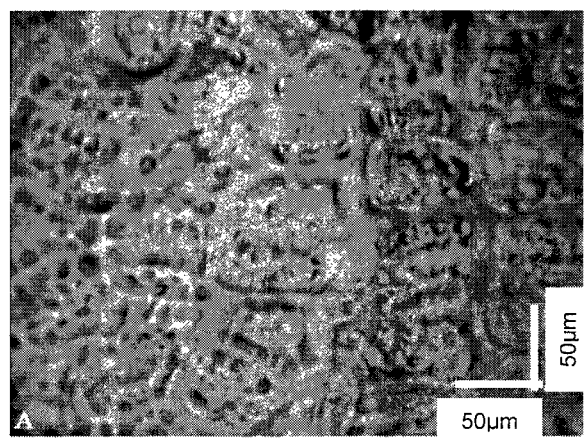
FIGS. 2A-2C. Research Grade Leica DMLM micrographs of uncoated (FIG. 2A), carnauba wax formulation-coated (FIG. 2B) and carnauba wax formulation-coated & brushed (FIG. 2C) red bell pepper samples.
Figure 2B:
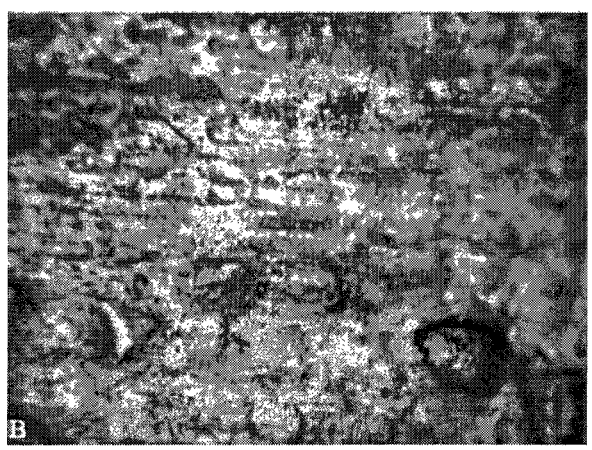
Figure 2C:

The thickness of the uncoated aluminum plate used in this study was 999±17 micron. After the plate was coated, a thickness of 1032±22 micron was measured and after brushing the coated plate, its thickness was 1015±19 micron. It is therefore contemplated that the wax-hydrocolloid coating thickness on a metal is approximately 30 micron, and that brushing the coated material decreases the coating thickness by half. Because a metal plate responds differently to the coating formulation as compared to the fruit, it is not conclusive that the thickness of the coating on a metal plate resembles the thickness of the fruit coating. Furthermore, the measurements which were performed on the plate could not be performed on a fruit sample for the following reasons: there is a large diversity between thicknesses of different peppers, different sizes of peppers have different surface areas on which the coating is spread, and postharvest fruit continues to carry out metabolic processes such as respiration, enzymatic activity etc. (MacRae et al., Planta, 188, 314-323, 1992). As a result, the thickness of the fruit sample changes with time and cannot be used for coating thickness measurements. However, from micrographs taken from surface area of uncoated, coated and coated & brushed pepper samples (FIGS. 2A-2C), it is evident that the thickness of the coating on pepper fruit diminishes when applying the brushing procedure. In FIG. 2A the surface cells silhouette can clearly be seen, where in FIG. 2B the cells' surface is covered by the coating. After the sample brushing, the thickness of the coating decreased as is evident by the silhouette of the surface cells which is visible once again together with the coating lair (FIG. 2C).

Example 4

Weight Loss—Effect of the Wax Weight Percentage (Test Group A)

The slopes and coefficient of determination ($R^2$) of weight loss as a function of storage time in peppers from treatment group (1) uncoated and coated by formulations comprising carnauba wax from the following treatment groups: (1) uncoated, coated with (2) formulation 1 (10% (w/w) carnauba formulation), and (3) coated with formulation 2 (15% (w/w) carnauba formulation), are summarized in table 5.

TABLE 5

Weigh loss rate of peppers coated by formulations comprising carnauba wax with different weight percentages (10 and 15% (w/w)).

| Treatment group | Formulation | % Carnauba wax | Weight loss rate per hour (%) | (SE) · $10^{-3}$ | ($R^2$) | Statistical significance |
|---|---|---|---|---|---|---|
| 1 | — | — | 0.11 | 4.14 | 0.99 | a |
| 2 | 1 | 10 | 0.10 | 5.11 | 0.99 | b |
| 3 | 2 | 15 | 0.08 | 4.01 | 0.99 | a |

The slopes indicate the weight-loss rate in each treatment. The fruit coated with formulation 2, having the highest wax content (15% (w/w)) among the carnauba wax formulations tested for the weight loss, had a significantly smaller slope (lower weight-loss rate) than the other two groups (p≤0.05). Its weight loss rate was 25% lower than that of the uncoated fruit, wherein the weight loss of formulation 2 (10% carnauba wax) was only 12% lower than that of the uncoated fruit. Therefore, it may be concluded that raising the wax content in the formulation above 10% (w/w) afforded significantly decreasing the weight loss of the coated fruit peppers.

The slopes and coefficient of determination ($R^2$) of weight loss as a function of storage time in peppers from treatment group (1) uncoated and coated by formulations comprising beeswax from the following treatment groups: (4) coated with formulation 4 (5% (w/w) beeswax formulation), (5) coated with formulation 5 (10% (w/w) beeswax formulation), (6) coated with formulation 6 (15% (w/w) beeswax formulation), and (7) coated with formulation 7 (20% (w/w) beeswax formulation), are summarized in table 6.

TABLE 6

Weigh loss rate of peppers coated by formulations comprising beeswax with different weight percentages (5, 10, 15 and 20% (w/w)).

| Treatment group | Formulation | % Beeswax | Weight loss rate per hour (%) | (SE) · $10^{-3}$ | ($R^2$) | Statistical significance |
|---|---|---|---|---|---|---|
| 1 | — | — | 0.052 | 1.41 | 1.00 | a |
| 4 | 4 | 5 | 0.033 | 1.33 | 0.99 | bc |
| 5 | 5 | 10 | 0.033 | 1.42 | 0.99 | bc |
| 6 | 6 | 15 | 0.028 | 1.19 | 0.99 | c |
| 7 | 7 | 20 | 0.027 | 1.31 | 0.99 | c |

The fruits coated with formulations 4 and 5, comprising 5% (w/w) and 10% (w/w) beeswax respectively demonstrated a decrease of the storage weigh loss of 37% compared to the uncoated fruit. Formulations 6 and 7, comprising higher beeswax content allowed reduction of 46% and 48% respectively in the weight loss of pepper fruits, compared to the uncoated fruits (p<0.05). Therefore, raising the wax content in formulations comprising beeswax decreased the weight loss of the coated peppers, wherein the formulations comprising wax concentration above 10% (w/w) allowed diminishing the weight loss by almost 50%.

Example 5

Weight Loss—Effect of the Wax Type and Brushing (Test Group B)

Figure 3:
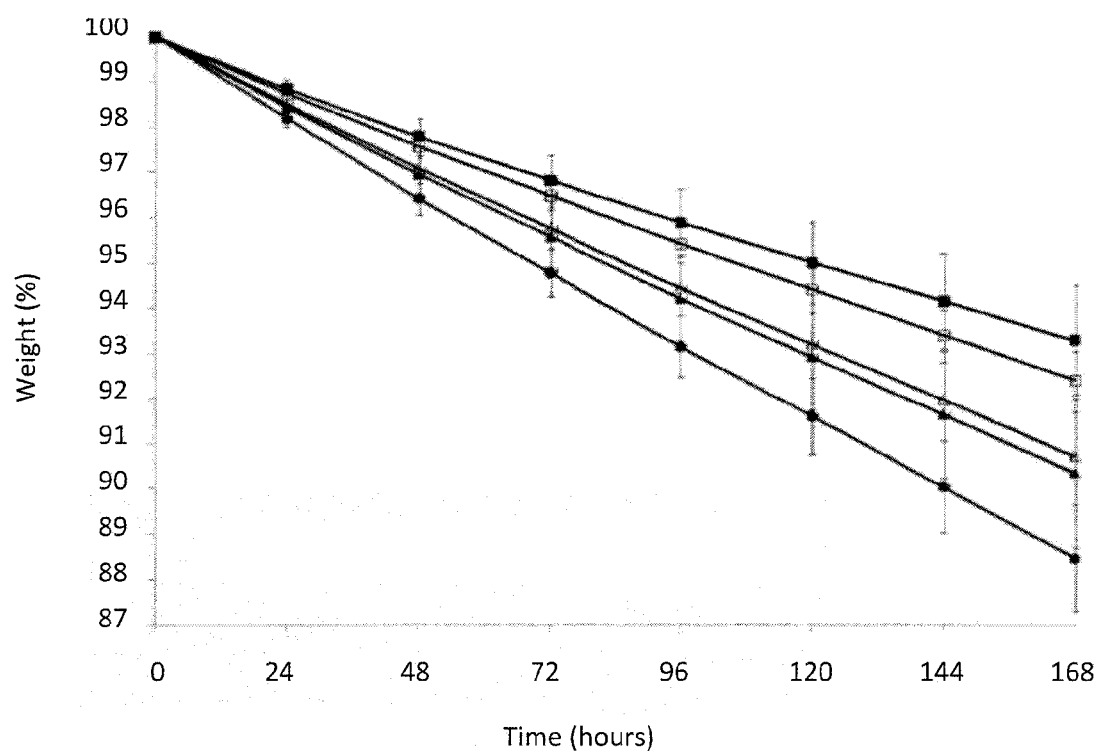
FIG. 3. Retained weight (%) in red bell peppers during 7 days of storage. Uncoated (●), coated with beeswax formulation (■), coated with beeswax formulation and then brushed (□), coated with carnauba wax formulation (▲), coated with carnauba wax formulation and then brushed (Δ).

The retained weight (%) of the pepper fruits from test group B (formulations 2 & 6) during 7 days of storage is presented in FIG. 3. Maalekuu et al. (J. Am. Soc. Horticultural Sci., 130, 735-741, 2005) established the linear relationship between the percentage of weight loss in peppers and elapsed time. Similar relations were found here. The slopes and coefficient of determination ($R^2$) of weight loss as a function of storage time in peppers from treatment group (1) uncoated and coated by formulations comprising 15% (w/w) carnauba wax or 15% (w/w) beeswax from the following treatment groups: (1) uncoated control, (2) coated with formulation 6 (15% (w/w) beeswax formulation), (3) coated with formulation 6 followed by brushing, (4) coated with formulation 2 (15% (w/w) carnauba wax formulation), and (5) coated with formulation 2 followed by brushing are summarized in table 7.

TABLE 7

Weigh loss rate of peppers coated by formulations comprising 15% (w) carnauba wax or 15% (w/w) beeswax, with and without brushing.

| Treatment group | Formulation | Brushing | Weight loss rate per hour (%) | (SE) · $10^{-3}$ | ($R^2$) | Statistical significance |
|---|---|---|---|---|---|---|
| 1 | — | − | 0.068 | 0.79 | 1.00 | a |
| 2 | 6 (carnauba) | − | 0.040 | 0.87 | 1.00 | d |
| 3 | 6 (carnauba) | + | 0.045 | 0.74 | 1.00 | c |
| 4 | 2 (beeswax) | − | 0.057 | 0.79 | 1.00 | b |
| 5 | 2 (beeswax) | + | 0.054 | 0.73 | 1.00 | b |

The slopes indicate the weight-loss rate in each treatment. The uncoated fruit had a significantly greater slope (higher weight-loss rate) than any other treatment, i.e. than any of the coated fruit (p≤0.0001). This demonstrates that coatings with either beeswax or carnauba wax, regardless of whether they are followed by brushing, reduce the weight-loss rate and contribute to shelf-life extension of peppers. The beeswax formulation resulted in the lowest weight loss, differing significantly from both carnauba wax treatments (p≤0.0001). Moreover, the beeswax-coated and brushed fruit showed a higher rate of weight loss than the beeswax-coated fruit without brushing (p≤0.05). This suggests that the brushing technique decreases the integrity of the coating, albeit only minimally because the beeswax-coated and brushed peppers still demonstrated a significantly lower weight-loss rate than controls. After 7 days in storage, the uncoated fruit lost almost twice the weight as compared to the weight lost by the beeswax-coated fruit. Moreover, the uncoated peppers lost over 5% of their initial weight after 72 hours, i.e. after 3 days at room temperature, whereas the peppers coated with the beeswax formulation only lost this amount after 144 hours (6 days). Thus, the beeswax coating inhibited pepper shriveling, retained its quality and doubled its shelf life. It is therefore concluded that the beeswax formulation was by far the most suitable formulation for shelf-life extension of red bell peppers.

Example 6

Weight Loss—Visual Appearance (Test Group B, Formulation 6)

Figure 4:
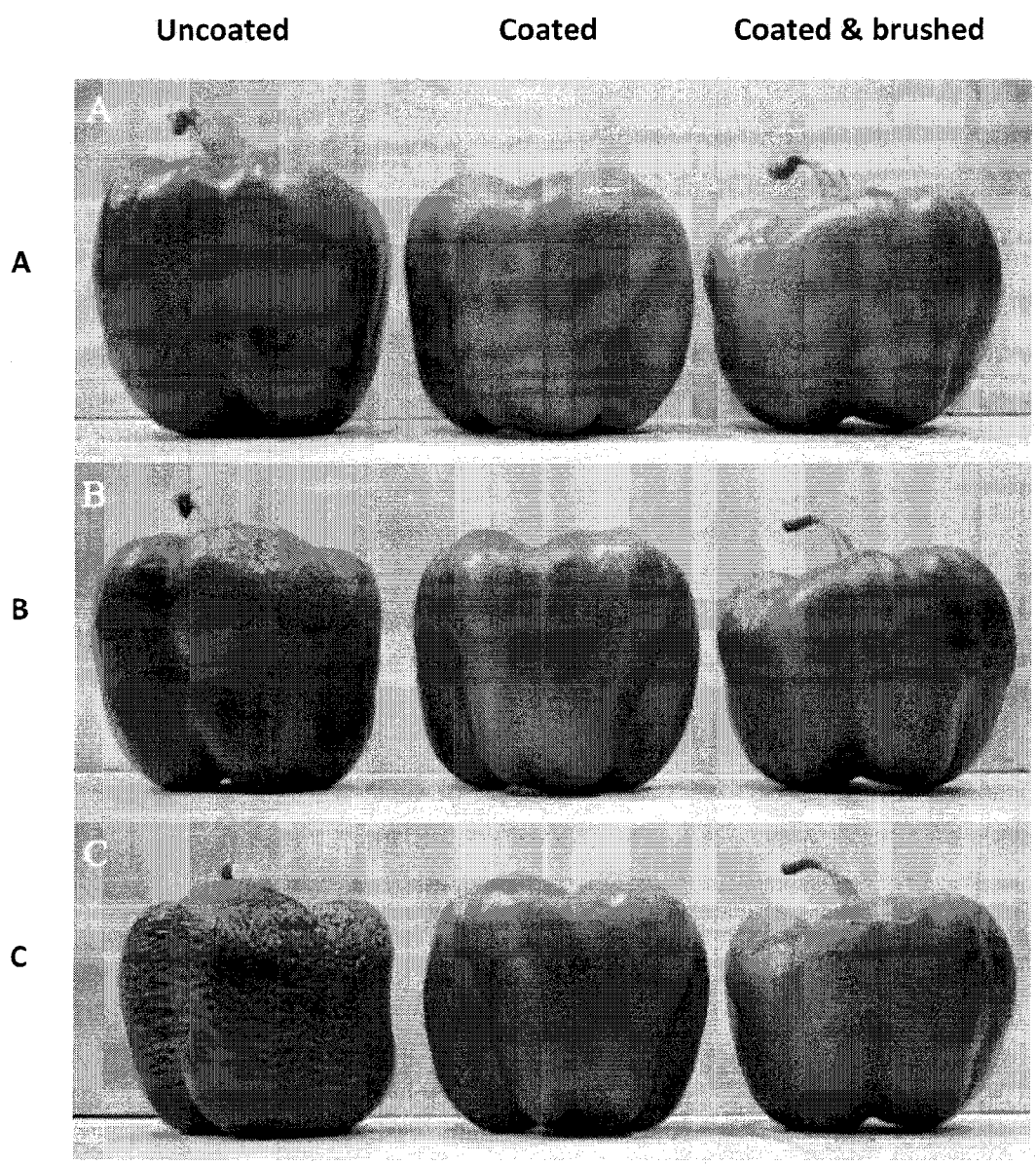
FIG. 4. Images of uncoated, beeswax formulation-coated, and beeswax formulation-coated and brushed red bell peppers after 1 day (panel A), 1 week (panel B) and 2 weeks (panel C) of storage at room temperature.
Figure 5A:
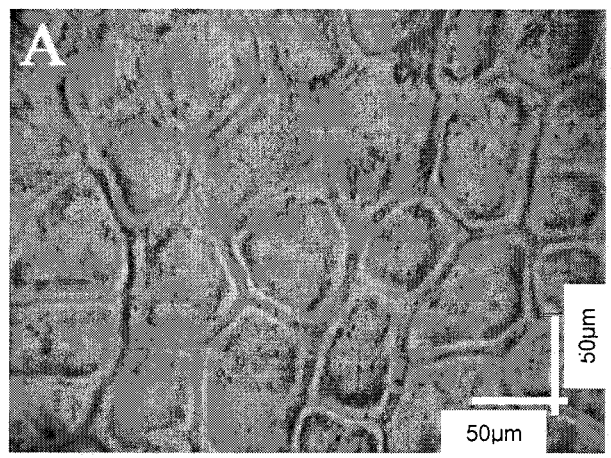
FIGS. 5A-5C. Light micrographs of uncoated (FIG. 5A), beeswax formulation-coated (FIG. 5B), and beeswax formulation-coated and brushed (FIG. 5C) red pepper samples (magnification ×20).
Figure 5B:
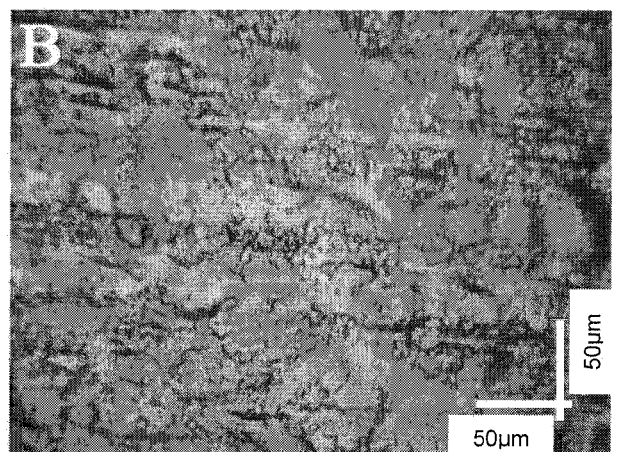
Figure 5C:
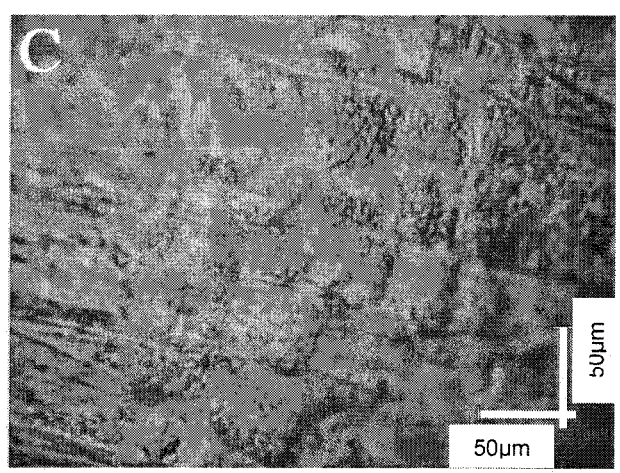

Differences in the appearance of the red bell peppers test group B (treatment groups: (1) uncoated control, (2) coated with formulation 6 (15% (w/w) beeswax formulation), and (3) coated with formulation 6 followed by brushing,)) during storage at room temperature are presented in FIG. 4. Senescence of the uncoated fruit clearly occurred much faster than in the treated fruit. After 1 week at room temperature (panel B), the uncoated peppers started to shrivel while the coated peppers maintained their "fresh" appearance. These differences in appearance were manifested during storage. After 2 weeks (panel C), the coated and brushed peppers also started to shrivel whereas the coated fruit retained a smooth surface. These results are consistent with the weight-loss rates shown in FIG. 3. The micrographs in FIGS. 5A-5C show the differences between the surface appearance of the peppers in each treatment (1, 2 & 3). In FIG. 5A, the pepper's cells can be easily observed, whereas in FIG. 5B the surface is covered by the coating and therefore the cells are less distinguishable, if at all. In FIG. 5C, slits are observed on the pepper's surface, supporting the assumption that brushing damages the coating's integrity.

Example 7

Gloss of Aluminum Plate (Formulation 3)

Figure 6A:
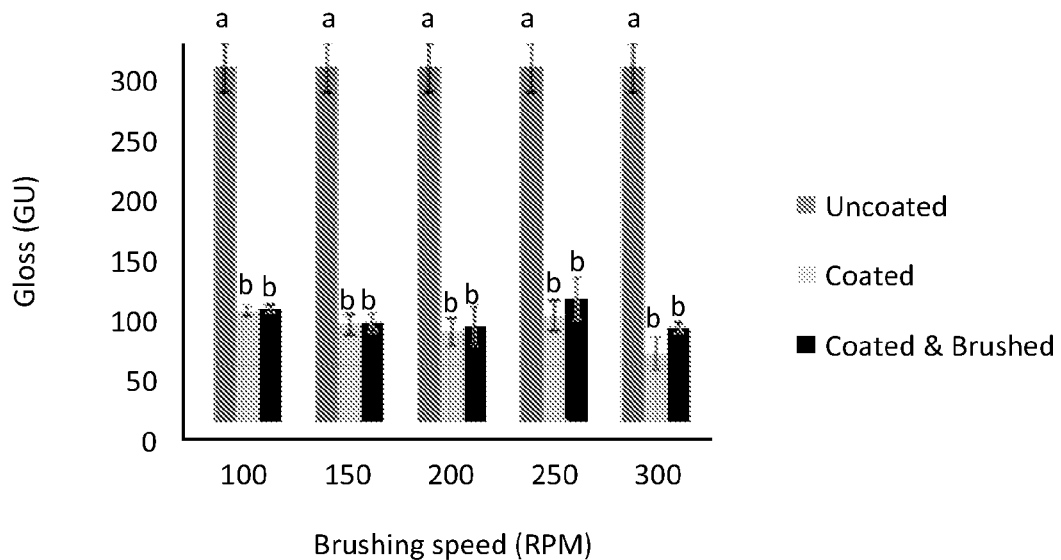
FIGS. 6A-6B.
Figure 6B:
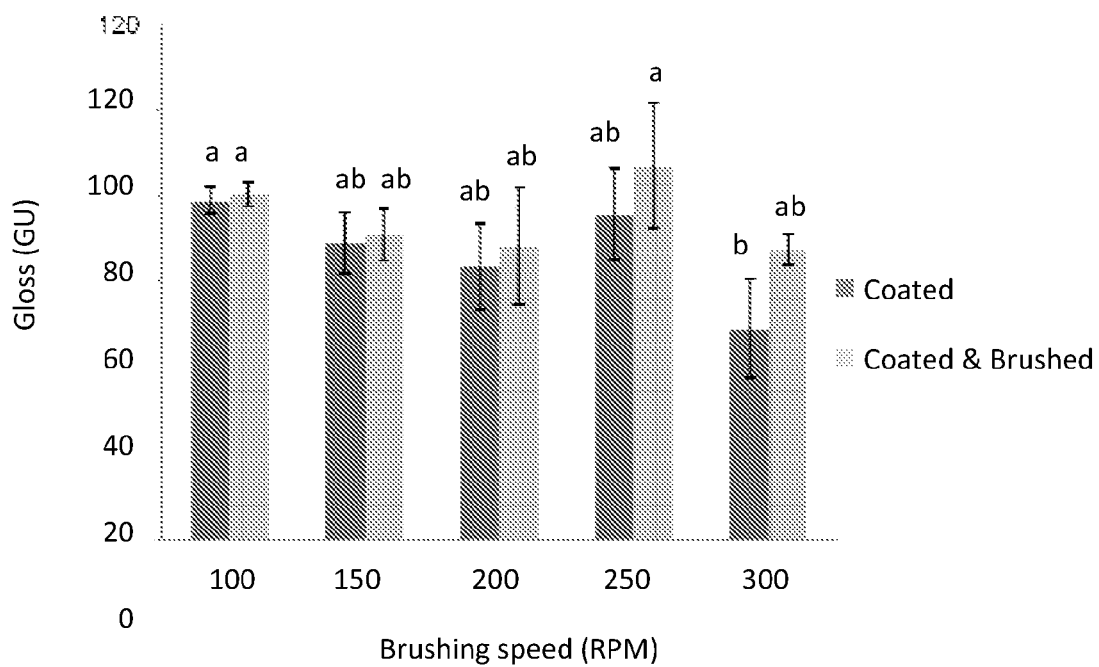
Figure 7A:
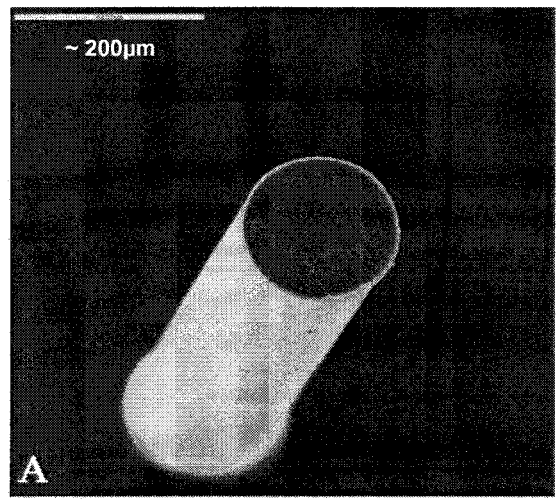
(FIG. 7A) Polyethylene ×2,200, (FIG. 7B) soft nylon ×2,200, (FIG. 7C) horse hair ×1,200, (FIG. 7D) horse hair ×2,200.
Figure 7B:
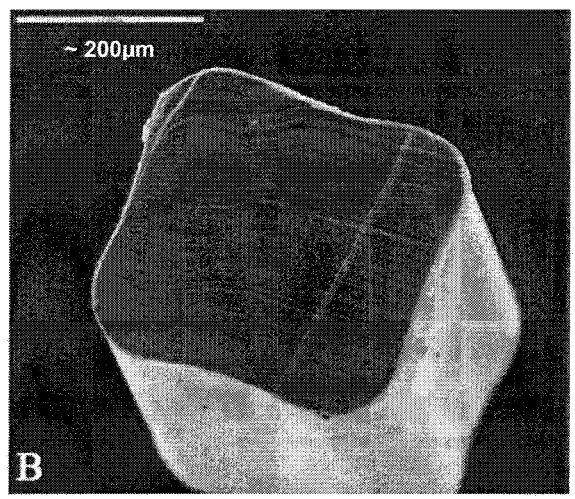
Figure 7C:
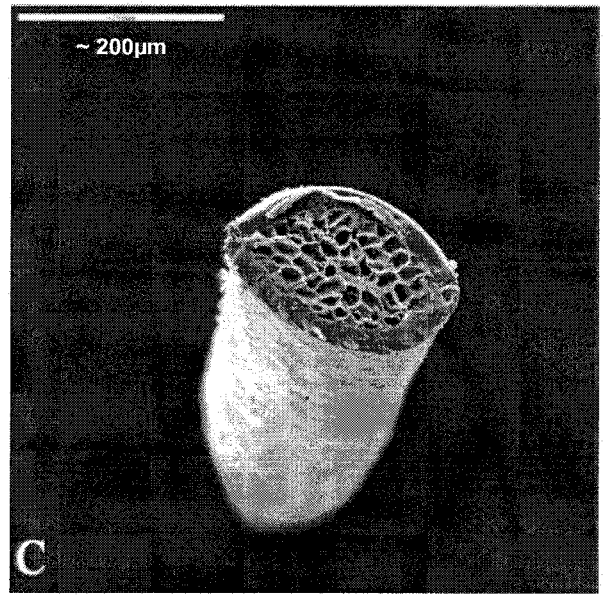
Figure 7D:
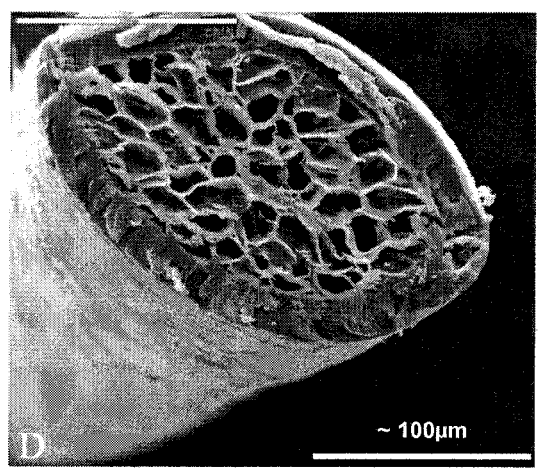

Aluminum is a very shiny chemical element. The gloss of the uncoated aluminum plate used in this study was 250±20 gloss units. After coating, the gloss of the plate extremely decreased to an average of 60±10 gloss units which is nearly 20% its gloss before coating. The brushing process in all brush types (horse hair, polyethylene and soft nylon) at brushing time intervals of 1 and 5 minutes, and all five brushing speeds (100, 150, 200, 250 and 300 rpm) increased the gloss of the plate but resulted in very minor and non-significant effect (FIGS. 6A-6B).

Example 8

Gloss of Pepper Fruit Samples (Test Group C)

Table 8 summarizes the average gloss of uncoated, coated and coated & brushed peppers. After hand coating of the pepper samples with formulation 3, comprising 18% carnauba wax, the gloss of the red bell pepper significantly diminishes. The average gloss of the untreated pepper samples was 13.2±1.5 gloss units in comparison to 3.7±0.95 gloss units after coating treatment. Namely, the coating diminishes the gloss of the coated commodity by a factor of ~3.6 (Down to ~30% of the initial gloss). Red bell pepper is known for its natural gloss which is attributed to sterol and wax natural coating composition (Nussinovitch et al., Lebensm.-Wiss. u.-Technol, 29:184-186, 1995). Surprisingly, where the time interval for brushing increased from 1 to 5 or 10 minutes, another phenomenon was observed as follows: at 1 minute, using horse hair brushes at 100 rpm, the recorded gloss values were 7.8±1.4, whereas after 5 or 10 minutes of brushing the recorded gloss values increased to 8.4±1.0 and 9.5±2.0, respectively. Thus, an increase in the time interval of polishing at the same speed and brush type resulted in an increase of the gloss values. It is noteworthy that at this brush type and brushing speed, no significant differences were observed when increasing the time intervals from 5 to 10 minutes. The highest gloss value measured (i.e. 9.5), although being lower in comparison to the value of uncoated pepper (i.e. 13.2), still represents a glossy surface that could be easily sold as the natural uncoated commodity. The highest contribution of the brushing procedure was observed at 300 rpm. At this brushing speed using the horse hair brush, increasing the brushing time interval to 10 minutes resulted in an observed gloss of 10.3±2.0 gloss values which represents an increased from ~30% back to ~80% of the initial gloss of the uncoated pepper.

When increasing the speed from 100 to either 200 or 300 rpm using polyethylene brushes at brushing time intervals of 1 to 10 minutes, a general increase in the gloss values was measured. The longer the brushing time intervals, the higher the gloss values that were measured. However, only brushing for 10 minutes resulted in a sensory accepted value of 8.4±1.7 gloss units. When increasing the speed from 100 to either 200 or 300 rpm using nylon brushes at brushing time intervals of 1 to 10 minutes, the gloss values have not changed significantly or showed a significant increase (Table 8).

TABLE 8

Average gloss of uncoated, coated and coated & brushed (after brushing red pepper samples at three brushing speeds (100, 200 and 300 rpm), three brushing time intervals (1, 5 and 10 min) and using three brush types (horse hair, polyethylene and soft nylon))

| Average gloss of coated peppers after brushing (GU)* | Brush type | Brushing time (min) | Brushing speed (rpm) | Average gloss of coated peppers before brushing (GU)* | Average gloss of uncoated peppers (GU)* |
|---|---|---|---|---|---|
| 10.32 ± 2.04a | Horse | 10 | 300 | 3.83 ± 0.32 | 12.72 ± 0.82 |
| 9.54 ± 2.03ab | Horse | 10 | 100 | 3.33 ± 0.12 | 12.74 ± 0.75 |
| 9.16 ± 0.59ab | Horse | 5 | 300 | 4.33 ± 0.29 | 11.49 ± 1.15 |
| 8.73 ± 2.52abc | Nylon | 5 | 300 | 4.17 ± 0.50 | 12.88 ± 0.48 |
| 8.39 ± 1.67abc | Polyethylene | 10 | 300 | 3.20 ± 0.10 | 13.74 ± 1.56 |
| 8.37 ± 1.05abc | Horse | 5 | 100 | 2.67 ± 0.06 | 10.42 ± 1.19 |
| 8.37 ± 3.02abc | Nylon | 5 | 100 | 3.60 ± 0.46 | 14.04 ± 1.48 |
| 8.29 ± 0.49abcd | Horse | 5 | 200 | 4.17 ± 0.15 | 12.94 ± 1.58 |
| 7.76 ± 1.42abcd | Horse | 1 | 100 | 2.87 ± 0.15 | 10.99 ± 1.54 |
| 7.67 ± 1.47abcd | Nylon | 5 | 200 | 2.73 ± 0.15 | 12.89 ± 0.76 |
| 7.47 ± 1.82abcd | Polyethylene | 1 | 200 | 2.93 ± 0.06 | 13.07 ± 1.24 |
| 7.33 ± 1.61abcd | Horse | 1 | 200 | 2.57 ± 0.06 | 7.33 ± 1.61 |
| 7.29 ± 0.57abcd | Nylon | 10 | 300 | 3.07 ± 0.15 | 14.60 ± 1.11 |
| 7.23 ± 1.21abcd | Horse | 10 | 200 | 4.67 ± 0.25 | 12.81 ± 1.41 |
| 6.81 ± 2.37abcd | Polyethylene | 1 | 300 | 3.07 ± 0.25 | 13.59 ± 0.88 |
| 6.49 ± 2.01abcd | Polyethylene | 5 | 300 | 2.47 ± 0.06 | 13.42 ± 0.94 |
| 6.41 ± 0.56abcd | Nylon | 1 | 300 | 2.50 ± 0.00 | 15.16 ± 2.17 |
| 6.16 ± 0.76abcd | Nylon | 10 | 200 | 2.57 ± 0.06 | 12.89 ± 1.04 |
| 6.13 ± 0.50abcd | Polyethylene | 1 | 100 | 2.33 ± 0.12 | 12.21 ± 1.04 |
| 6.06 ± 1.84abcd | Polyethylene | 10 | 200 | 2.43 ± 0.21 | 12.71 ± 0.66 |
| 6.03 ± 0.34abcd | Horse | 1 | 300 | 2.93 ± 0.42 | 13.59 ± 1.51 |
| 5.89 ± 0.78abcd | Nylon | 1 | 200 | 2.57 ± 0.15 | 13.66 ± 0.81 |
| 5.49 ± 0.50abcd | Nylon | 1 | 100 | 2.53 ± 0.06 | 13.96 ± 0.98 |
| 5.18 ± 1.11bcd | Nylon | 10 | 100 | 2.87 ± 0.12 | 13.84 ± 0.97 |
| 4.26 ± 0.50bcd | Polyethylene | 5 | 200 | 3.23 ± 0.25 | 13.09 ± 0.74 |
| 3.97 ± 0.51cd | Polyethylene | 10 | 100 | 2.97 ± 0.15 | 12.50 ± 0.29 |
| 3.38 ± 0.54d | Polyethylene | 5 | 100 | 4.83 ± 0.12 | 14.27 ± 1.58 |

* Each result is the average of 9 determinations ± SD. Difference are significant at $p \leq 0.05$.

Upon general comparison between different brush types at different brushing speed and brushing time intervals it is evident that the horse brush is the most efficient type of brush with nylon and polyethylene brushes being less efficient in restoring gloss to the peppers. Without being bound by any theory or mechanism of action, it is contemplated that the porosity of the horse hair brush as evident from its cross-section scanning electron micrograph, enables to absorb the fluidity smeared wax-hydrocolloid formulation resulting in a better application of the coating on the pepper surface. Both the synthetic nylon and polyethylene brushes, contain fibers that are not porous. Accordingly, these brushes are not capable of absorbing any coating fluid/preparation and merely afford its smearing on the surface (FIGS. 7A-7D).

Upon brushing of the coated commodity an increase in the gloss of the coated fruit in comparison with the coated non-glossy surface (3.7 gloss units in average) was obtained. This increase was not sufficient to restore the natural gloss values of the pepper skin. At same brushing time interval (1 minute) and using the same brush type (horse hair), the following values of gloss units were obtained: 7.7±1.4 at brushing speed of 100 rpm, 7.3±1.6 at brushing speed of 200 rpm and 6.0±0.3 at brushing speed of 300 rpm. These values of are 1.6 to 2.1 times larger than the values of coated non-glossy pepper (Table 8).

Figure 8:
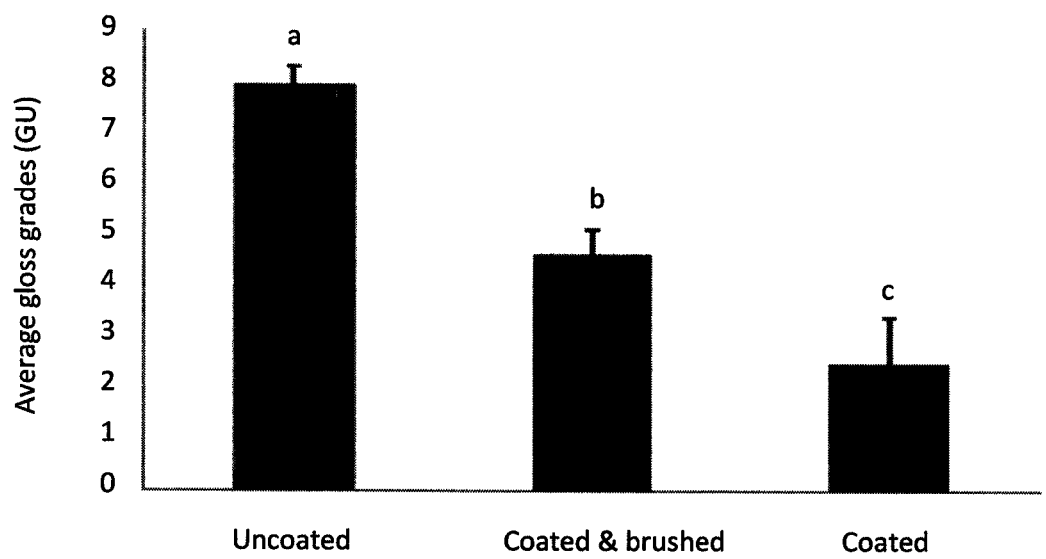
FIG. 8. Average gloss grades of uncoated, carnauba wax formulation-coated and carnauba wax formulation-coated & brushed red peppers that were ranked by the sensory evaluation panel.

The results presented in FIG. 8 show that each treatment provides a significant difference in gloss values. The uncoated peppers showed the highest gloss values as compared to the other treated peppers. The peppers coated with the formulation comprising carnauba wax were the least glossy, and the peppers coated with the formulation comprising carnauba wax that underwent brushing treatment showed nearly doubled gloss valued as compared to the coated peppers that were not subjected to brushing treatment. It is thus concluded that post-coating brushing treatment provides a significantly high increase in the fruit's gloss. Hence, by using the brushing procedure, peppers with improved properties and fewer damages to their appearance may be obtained.

Example 9

Gloss of Pepper Fruits (Test Group D)

Figure 9:
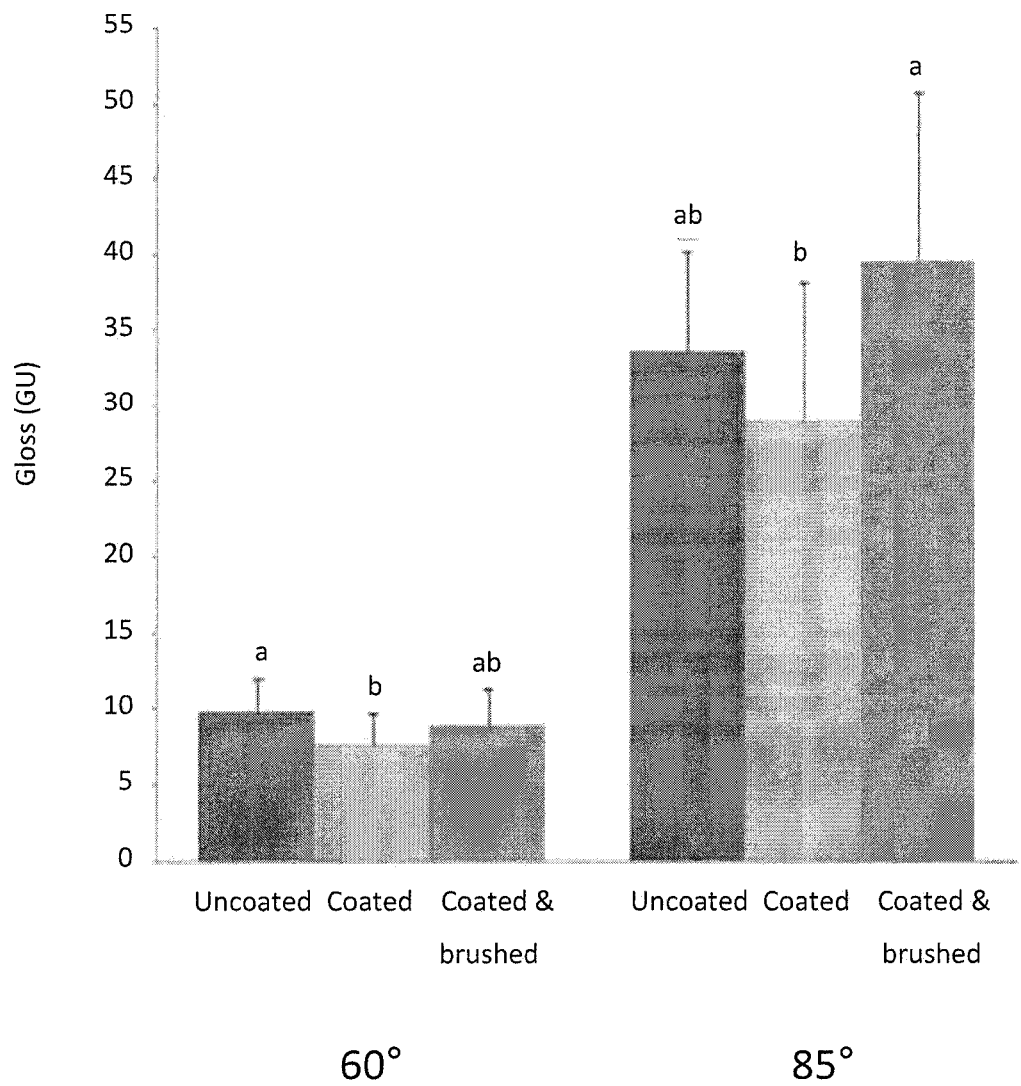
FIG. 9. Gloss of uncoated, beeswax formulation-coated, and beeswax formulation-coated and brushed red bell peppers at 60° and 85° angles. Different letters within the same angle indicate significant differences between treatments ($p \leq 0.01$).

The gloss of pepper fruits coated with formulation 6 comprising 15% beeswax and of the coated peppers which underwent following brushing was measured. The results of the surface glossmeter measurements are presented in FIG. 9. Measurements taken at both 60° and 85° angles demonstrated that the natural gloss of the pepper decreases after coating with the beeswax formulation and increases after brushing to a level which is not significantly different from the natural gloss of the uncoated pepper ($p \leq 0.01$). The gloss measurements using the curved-surface glossmeter showed similar results. The highest value at full width at half height was detected for the coated fruit (28.2±1.0), which was significantly different ($p \leq 0.0001$) from the value of the coated and brushed peppers (23.9±1.1). It is contemplated that the width at half height of the goniophotometric curve indicates the inverse of the gloss level, i.e., the larger the width at half height, the lower the measured gloss value. The increase in gloss as a result of brushing was in agreement with the enhanced gloss of polished peppers as compared to unpolished ones due to the regenerated structure of the epicuticular wax layer (Charles et al., Postharvest Bio. Technol., 47, 21-26, 2008). Thus, even though the highest gloss values were achieved for uncoated fruits, coating with 15% (w/w) formulation decreased the peppers' gloss by ~25% while brushing increased it again by ~15% resulting in a mere 10% reduction in its natural gloss.

Example 10

Roughness (Test Group D)

Figure 10:
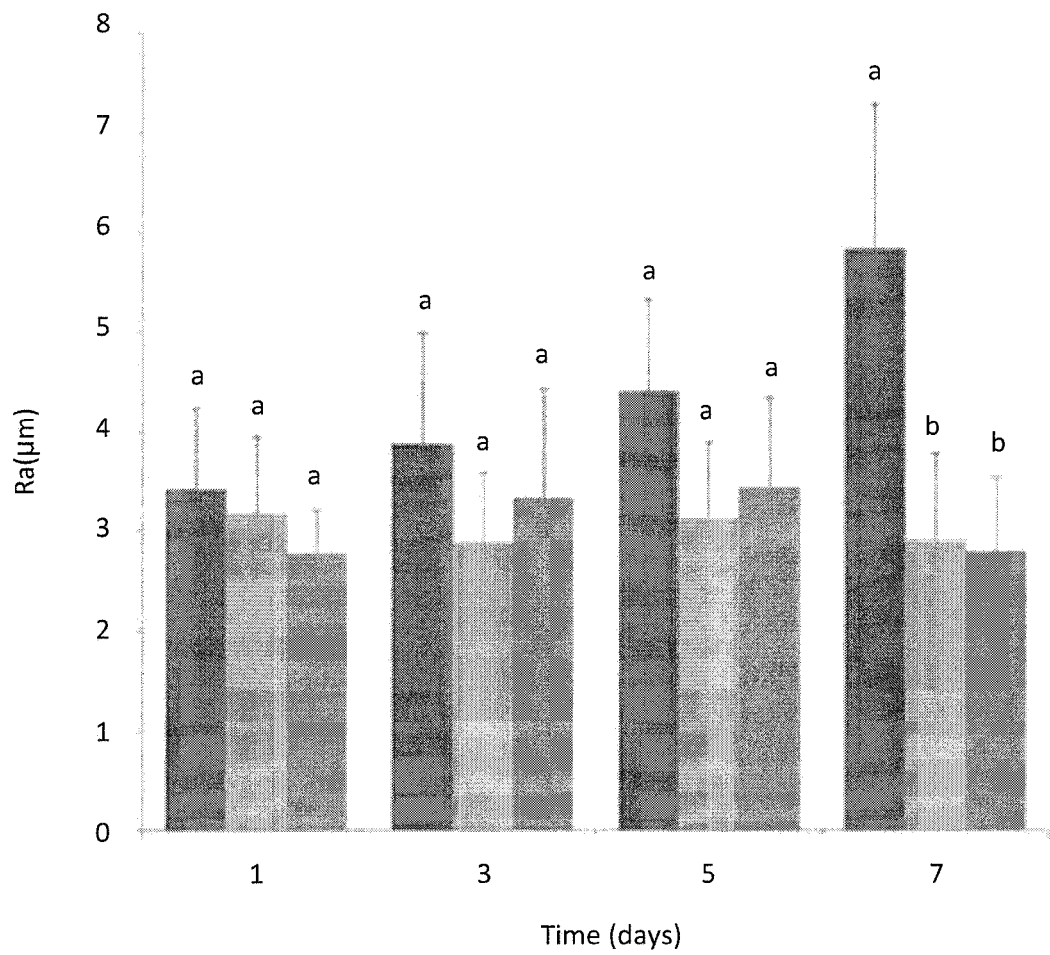
FIG. 10. Roughness ($R_a$) of uncoated (left), beeswax formulation-coated (middle), and beeswax formulation-coated and brushed (right) red bell peppers during 7 days of storage at room temperature. Different letters within a sampling day indicate significant differences between treatments ($p \leq 0.0001$).
Figure 11A:
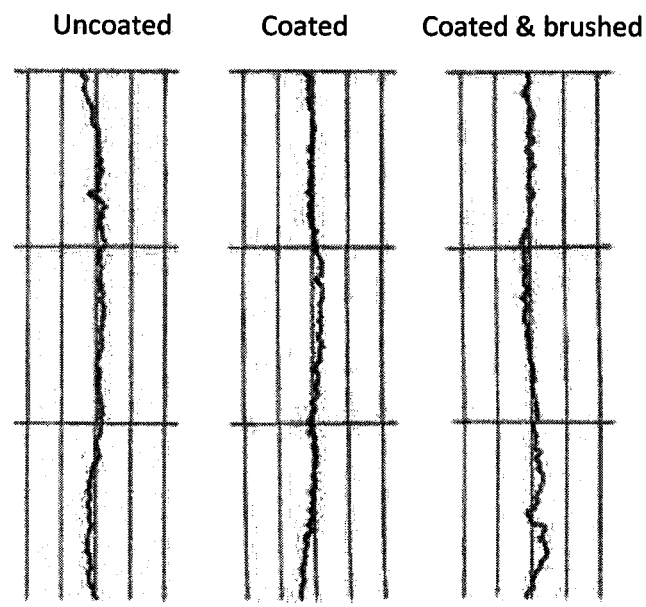
FIGS. 11A-11B. Surface-roughness profile of uncoated, beeswax formulation-coated, and beeswax formulation-coated and brushed red bell peppers after 1 (FIG. 11A) and 7 (FIG. 11B) days of storage at room temperature.
Figure 11B:
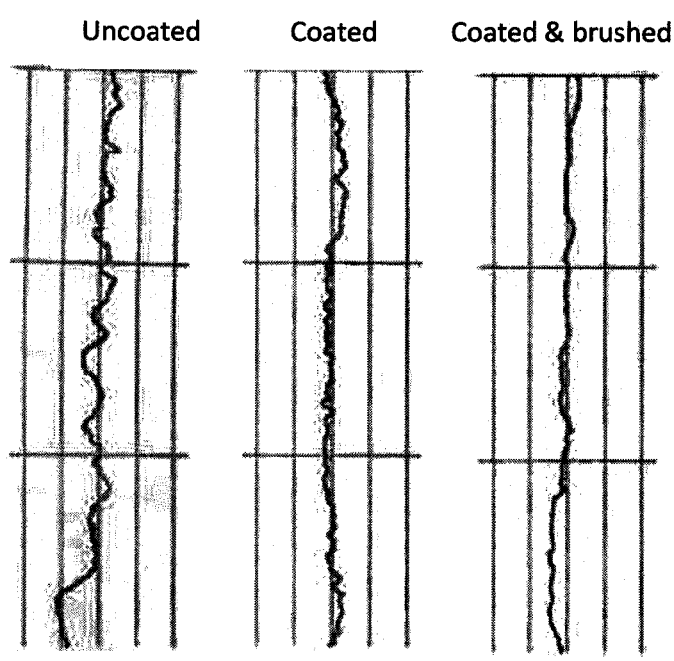

As a result of the high rate of weight loss of the uncoated fruit during storage (FIG. 3), its surface roughness increased rapidly with time in comparison to the two other coated groups (treatment groups (2) coated with formulation 6 (15% (w/w) beeswax formulation) and (3) coated with formulation 6 followed by brushing)) (FIG. 10). After 7 days of storage, the average $R_a$ and $R_z$ values of the uncoated peppers were 5.8±1.5 and 19.4±7.3 μm, respectively, significantly higher than the $R_a$ and $R_z$ values of the coated peppers (2.9±0.9 and 12.3±2.7 μm, respectively) and coated and brushed peppers (2.8±0.8 and 11.8±2.1 μm, respectively) ($p \leq 0.05$). FIGS. 11A and 11B show the surface-roughness profiles of the red bell peppers from the three treatments, namely uncoated, coated, and coated and brushed, after 1 and 7 days of storage, respectively. On the first day of storage, all three roughness profiles were similar. However, after 7 days, the uncoated profile (and surface of the pepper) was rougher than the profiles of treated peppers. These results also indicate that the beeswax-coating formulation slowed the peppers' senescence process and thus extended their shelf life.

Example 11

Color (Test Group F)

Red bell peppers change their color during ripening due to a decrease in the major chloroplast pigment, chlorophyll, concomitant with a rise in the levels of various carotenoids, resulting in a deep red color in the fully ripe peppers (Ha et al., J. Exp. Botany, 58, 3135-3144, 2007). During the first 3 days of storage, three treatments groups ((1) uncoated control, (2) coated with formulation 6 (15% (w/w) beeswax formulation), and (3) coated with formulation 6 followed by brushing,) showed an increase in a* and b* values: for the uncoated fruit, from 21.6±1.8 to 28.1±2.0 and from 10.5±1.5 to 14.1±1.6, respectively; for the beeswax-coated pepper from 18.9±2.0 to 28.7±2.3 and from 10.0±2.8 to 16.1±1.2, respectively; for the beeswax-coated and brushed fruit from 19.4±3.3 to 23.8±1.7 and from 11.8±1.5 to 11.8±1.9, respectively. From day 3, these levels remained constant (measurements every 24 hours) until day 7 of storage. L* did not show any changes in any treatment during storage, and had an average value of 33.2±1.2. These results, collected during the 7 days of storage, showed no significant differences in color change among the three treatments ($p \leq 0.0001$). Therefore, the beeswax coating formulation did not affect the color of the pepper from its natural change during the ripening process.

Example 12

Mechanical Properties (Test Group D)

Figure 12:
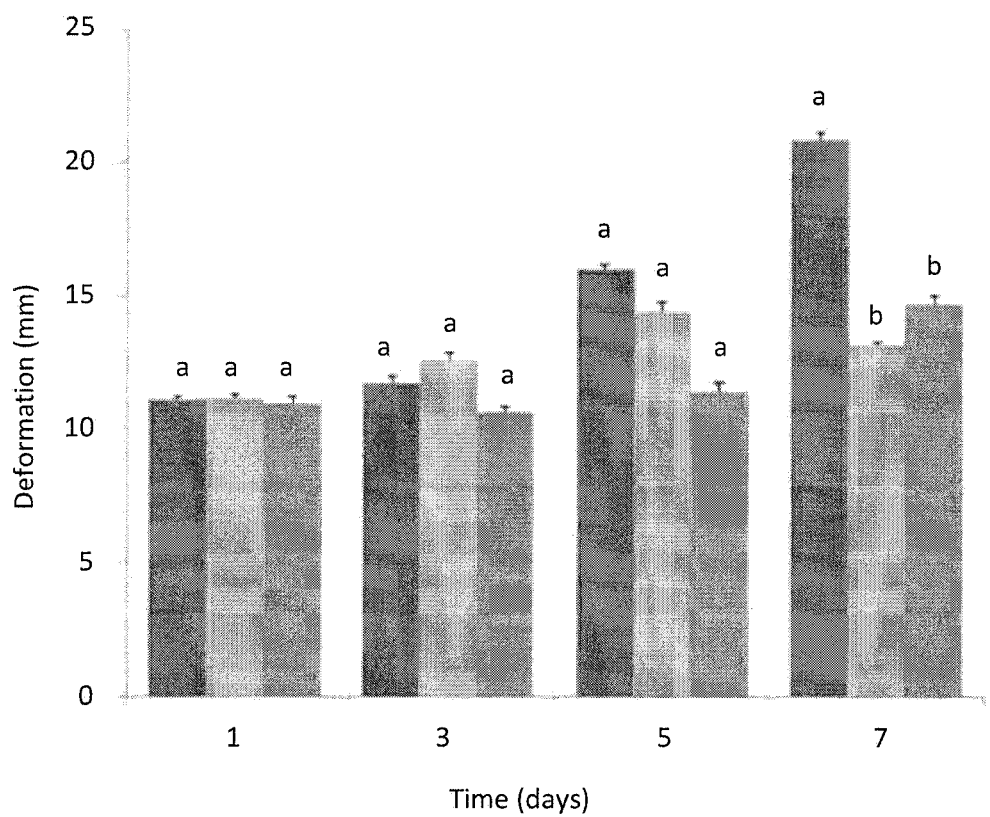
FIG. 12. Deformation at puncture during storage of uncoated (left), beeswax formulation-coated (middle), and beeswax formulation-coated and brushed (right) red bell peppers. Different letters within a sampling day indicate significant differences between treatments ($p \leq 0.001$).

The force at puncture was similar for treated and untreated peppers. Uncoated, coated with beeswax formulation, and coated with 15% (w/w) beeswax formulation and then brushed values that were obtained are 13.3±1.8 N, 13.6±0.8 N and 13.5±0.8 N, respectively. These values did not change significantly during 7 days of storage ($p < 0.0001$). However, the deformation at puncture increased during storage: the uncoated fruit went through the biggest change, resulting in a significantly higher ($p < 0.001$) deformation (20.8±2.4 mm) on day 7 of storage, relative to the coated (13.1±2.7 mm) and coated and brushed (14.7±2.1) fruit (FIG. 12). These results demonstrate that the uncoated fruits, after 7 days at 20° C. and 50% RH, were less rigid than the coated ones. Hence, coated fruits are stiffer than the uncoated ones and coating is shown to preserve the fruit's mechanical properties, resulting in extended shelf life.

Example 13

Simulations of Storage and Marketing Conditions (Test Groups G and H)

Groups G and H both showed a significantly higher percentage of weight-loss of untreated vs. 15% (w/w) beeswax formulation coated fruit after storage at 7° C. and 95% RH (p≤0.0001). After 3 weeks, weight loss of the uncoated fruit in group G amounted to 3.0±0.4%, compared to 2.4±0.4% and 2.4±0.5% in the coated and coated and brushed fruits, respectively. In group H, after 5 weeks of storage, the weight loss of the uncoated fruit amounted to 6.2±1.3%, compared to 3.4±0.5% and 3.5±0.9% for the coated and coated and brushed peppers, respectively. The percentage of weight-loss, which is mainly attributed to loss of water, of the coated peppers was far lower than other experiments showing a water loss of over 10% for coated peppers after 21 days of cold storage (Ozden et al., Euro. Food Res. Technol., 214, 320-326, 2002). After additional 3 days at 20° C. and 75% RH, the uncoated, coated, and coated and brushed fruits from group G lost an additional weight of 1.8±0.3%, 1.3±0.2% and 1.4±0.3%, respectively. For group H, after 3 days at 20° C. and 75% RH (following 5 weeks at 7° C. and 95% RH), the uncoated, coated, and coated and brushed peppers lost an additional weight of 1.8±0.4%, 1.0±0.2% and 1.0±0.2% of their respective weights. Thus, after 5 weeks of cool storage, the uncoated fruit lost 6.2±1.3% of its initial weight and was already shriveled and soft, while the coated and coated and brushed fruit lost only 3.4±0.5% and 3.5±0.9% of their initial weights, respectively, and maintained their "fresh" appearance and firmness.

Example 14

Sensory Evaluation (Formulations 2 and 6)

In both the initial taste and taste after storage evaluations, 60% of the panel members could not distinguish between the coated and uncoated fruit. In the second taste test, the panel members were also asked to note any specific taste differences between the samples: no off-flavors were detected for any of the treated peppers. The gloss evaluation results were in agreement with the physical measurements, i.e., the panelists determined that the beeswax and carnauba wax coating decreased the peppers' gloss while the brushing increased it to a level that was not noticeably different from the natural gloss. The firmness evaluation showed that after 7 days of storage, the treated peppers (coated by formulation 2 and formulation 6) were significantly firmer than the untreated ones (p<0.0001). In the final sensory test, no uncoated peppers were chosen; 40% of the chosen peppers were coated and 60% were coated and brushed. These results demonstrate that consumers tend to prefer the coated peppers, and in particular the coated and brushed peppers, over their uncoated counterparts.

The novel formulations of the present invention contribute to extending the pepper's shelf life. In addition, a special brushing procedure can increase the coated fruit's gloss following its decrease as a result of the coating process.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The invention claimed is:

1. A method for reducing the weight loss and preserving the natural gloss of a post-harvest edible plant matter comprising:
    the step of applying to the surface of the plant matter a composition comprising:
    a. an edible wax having a melting temperature lower than about 700C;
    b. a hydrocolloid polymer comprising a non-gelling hydrocolloid polymer;
    c. a fatty acid;
    d. an emulsifier; and
    e. water;
    thereby coating the edible plant matter with the composition, which preserves the natural gloss of the plant matter;
    drying the coating of the edible plant matter; and
    brushing the dried coated edible plant matter for about 1 to about 10 min;
    wherein the edible wax is present in a weight percent ranging from 10% to 25% of the total weight of said composition.

2. The method of claim 1, wherein the edible plant matter is selected from the group consisting of peppers, eggplants cherries, berries, plums and persimmons.

3. The method of claim 1, wherein the edible wax is selected from the group consisting of an animal wax, insect wax, microcrystalline wax and paraffin wax.

4. The method of claim 1, wherein the edible wax is present in a weight percent ranging from about 15% to about 25% of the total weight of the composition.

5. The method of claim 1, wherein the hydrocolloid polymer is selected from the group consisting of locust bean gum (LBG), guar gum, gum Arabic, xanthan gum, gum tragacanth, and mixtures thereof.

6. The method of claim 1, wherein the fatty acid is selected from the group consisting of oleic acid, stearic acid, palmitic acid, lauric acid, myristic acid, behenic acid, isostearic acid, and mixtures thereof.

7. The method of claim 1, wherein the emulsifier is selected from the group consisting of morpholine, ammonia, lecithin, ethylene glycol monostearate, ammonium lauryl sulfate, sodium steroyl-2-lactylate, potassium oleate, propylene glycol monostearate, sodium alkyl sulfate, polyglycol, and mixtures thereof.

8. The method of claim 1, wherein the composition is applied to the surface of the plant matter when the temperature of the composition is from about 35° C. to about 50° C.

9. The method of claim 1, wherein the brushing is performed using a brush comprising natural fibers.

10. The method of claim 1, wherein the brushing is performed at a brushing speed of about 100 rounds per minute (rpm) to about 300 rpm.

11. The method of claim 1, wherein
a. the edible wax is beeswax, which is present in a weight percent of 10%-25%;
b. the hydrocolloid polymer is present in a weight percent of up to 1%;
c. the fatty acid is present in a weight percent of 0.2%-10%;
d. the emulsifier is present in a weight percent of 0.1%-15%; and
e. water is present in a weight percent of 49%-89% of the total weight of the composition.

12. The method of claim 1, wherein the edible wax is a beeswax.

\* \* \* \* \*

UNITED STATES PATENT AND TRADEMARK OFFICE
CERTIFICATE OF CORRECTION

PATENT NO.        : 9,648,890 B2  
APPLICATION NO.   : 14/387242  
DATED             : May 16, 2017  
INVENTOR(S)       : Amos Nussinovitch Page 1 of 1

It is certified that error appears in the above-identified patent and that said Letters Patent is hereby corrected as shown below:

In the Claims

Column 32, Claim 1, Lines 21-23:  
Delete "...lower than about 700C; b. a hydrocolloid..."  
And replace with -- ...lower than about 70°C; b. a hydrocolloid... --

Signed and Sealed this
Twentieth Day of February, 2018

Andrei Iancu
*Director of the United States Patent and Trademark Office*